US012580078B2

(12) United States Patent
Lee et al.

(10) Patent No.: US 12,580,078 B2
(45) Date of Patent: Mar. 17, 2026

(54) METHOD, SERVER, AND SYSTEM INTELLIGENT VENTILATOR MONITORING USING NON-CONTACT AND NON-FACE-TO-FACE

(71) Applicant: UIF (University Industry Foundation), Yonsei University, Seoul (KR)

(72) Inventors: Su Hwan Lee, Seoul (KR); Kyu Bom Kim, Seoul (KR); Kyu Seok Kim, Seoul (KR); Bon Tack Koo, Seoul (KR); Yeonkyeong Kim, Seoul (KR)

(73) Assignee: UIF (UNIVERSITY INDUSTRY FOUNDATION), YONSEI YOUNVERSITY, Seoul (KR)

( * ) Notice: Subject to any disclaimer, the term of this patent is extended or adjusted under 35 U.S.C. 154(b) by 82 days.

(21) Appl. No.: 18/534,991

(22) Filed: Dec. 11, 2023

(65) Prior Publication Data

US 2024/0194337 A1     Jun. 13, 2024

(30) Foreign Application Priority Data

Dec. 12, 2022    (KR) ........................ 10-2022-0172338
Feb. 16, 2023    (KR) ........................ 10-2023-0020781

(51) Int. Cl.
*G16H 40/67*          (2018.01)
(52) U.S. Cl.
CPC ................................... *G16H 40/67* (2018.01)
(58) Field of Classification Search
None
See application file for complete search history.

(56) References Cited

U.S. PATENT DOCUMENTS

2007/0149862 A1*  6/2007  Pipke ..................... A61B 5/318
                                                        703/11
2009/0234262 A1*  9/2009  Reid, Jr. .............. A61B 5/0022
                                                        600/595
2011/0041850 A1   2/2011  Vandine et al.
(Continued)

FOREIGN PATENT DOCUMENTS

EP           1586344          10/2010
KR    10-2014-0051570          5/2014
(Continued)

OTHER PUBLICATIONS

Marcin Bajer et al., "Building an IoT Data Hub with Elasticsearch, Logstash and Kibana", 2017 5th International Conference on Future Internet of Things and Cloud Workshops, Aug. 2017.
(Continued)

*Primary Examiner* — John P Go
(74) *Attorney, Agent, or Firm* — LEX IP MEISTER, PLLC

(57)          ABSTRACT
Provided is a method of operating an integrated monitoring server operated by at least one processor, the method including: receiving waveform-type respiratory mechanics information in real time from a ventilator of a patient that is installed at a remote location, and transmitting the real-time received waveform-type respiratory mechanics information to a hospital system connected to the server through a dedicated line or mobile terminals of medical personnel connected to the server through an internet.

28 Claims, 17 Drawing Sheets

(56)                    References Cited

U.S. PATENT DOCUMENTS

| | | | | |
|---|---|---|---|---|
| 2012/0083675 A1* | 4/2012 | el Kaliouby | ........... | A61B 5/165 |
| | | | | 600/301 |
| 2013/0199533 A1* | 8/2013 | Steinhauer | ........ | A61M 16/1005 |
| | | | | 128/204.23 |
| 2014/0000609 A1* | 1/2014 | Steinhauer | ............. | G16H 40/67 |
| | | | | 128/204.23 |
| 2014/0048072 A1* | 2/2014 | Angelico | ........... | A61M 16/026 |
| | | | | 128/204.23 |
| 2017/0239432 A1 | 8/2017 | Delangre et al. | | |
| 2018/0101646 A1* | 4/2018 | Lloyd | .................... | G16H 10/60 |
| 2021/0090547 A1* | 3/2021 | Ping | ........................ | G10L 13/02 |
| 2022/0189609 A1 | 6/2022 | Peake et al. | | |

FOREIGN PATENT DOCUMENTS

| | | | | | |
|---|---|---|---|---|---|
| KR | 10-1780781 | 9/2017 | | | |
| KR | 10-2309022 | 10/2021 | | | |
| KR | 10-2376188 | 3/2022 | | | |
| WO | 2019/094736 | 5/2019 | | | |
| WO | WO-2022146057 A1 * | 7/2022 | ............. | G06N 3/042 |
| WO | WO-2022153329 A1 * | 7/2022 | ............. | G16H 15/00 |

OTHER PUBLICATIONS

Jeff Vanden Berghe et al., "An adaptive noise canceller for hearing aids using two nearby microphones", J. Acoust. Soc. Am. 103 (6), Jun. 1998.

Jürgen Tchorz et al., "SNR Estimation Based on Amplitude Modulation Analysis With Applications to Noise Suppression", IEEE Transactions on Speech and Audio Processing, vol. 11, No. 3, May 2003.

Wendy L. Wright, "Multimodal monitoring in the ICU: When could it be useful?", Journal of the Neurological Sciences 261 (2007) 10-15, Jun. 4, 2007, doi:10.1016/j.jns.2007.04.027.

Guoshen Yu et al., "Audio Denoising by Time-Frequency Block Thresholding", IEEE Transactions on Signal Processing, vol. 56, No. 5, May 2008.

Bhavesh Popat et al., "Invasive and non-invasive mechanical ventilation", Medicine, Jun. 2012; 40(6): 298-304, May 18, 2012.

Arthur S. Slutsky, M.D. et al., "Ventilator-Induced Lung Injury", The New England Journal of Medicine, Nov. 28, 2013;369(22):2126-36. doi: 10.1056/NEJMra1208707.

Abraham Bohadana, M.D. et al., "Fundamentals of Lung Auscultation", The New England Journal of Medicine, Feb. 20, 2014;370(8):744-51. doi: 10.1056/NEJMra1302901.

Molly M. McNett et al., "International Multidisciplinary Consensus Conference on Multimodality Monitoring: ICU Processes of Care", Neurocrit Care (2014) 21:S215-S228, Sep. 11, 2014, DOI 10.1007/s12028-014-0020-x.

Marcin Bajer et al., "Building an IoT Data Hub with Elasticsearch, Logstash and Kibana", 2017 5th International Conference on Future Internet of Things and Cloud Workshops, Aug. 2017.

Thach Lam, MD et al., "Continuous Pulse Oximetry and Capnography Monitoring for Postoperative Respiratory Depression and Adverse Events: A Systematic Review and Meta-analysis", Anesth Analg., vol. 125, No. 6, Dec. 2017, doi: 10.1213/ANE.0000000000002557.

Seul Mi Lee et al., "Effective Tidal Volume for Normocapnia in Very-Low-Birth-Weight Infants Using High-Frequency Oscillatory Ventilation", Yonsei Med J Jan. 2018;59(1):101-106, Nov. 29, 2017, https://doi.org/10.3349/ymj.2018.59.1.101.

James M. Walter, MD et al., "Invasive Mechanical Ventilation", South Med J. Dec. 2018 ; 111(12): 746-753. doi:10.14423/SMJ.0000000000000905.

Minzhong Zhang et al., "Cluster Function Extension of TCP Server Based on Apache Mina", 2018 2nd IEEE Advanced Information Management,Communicates,Electronic and Automation Control Conference(IMCEC 2018), May 2018.

Vitaly Herasevich, MD, PhD, FCCM et al., "Tele-ICU Technologies", Crit Care Clin 35 (2019) 427-438, Apr. 8, 2019.

Han Wu et al., "Performance Prediction for the Apache Kafka Messaging System", 2019 IEEE 21st International Conference on High Performance Computing and Communications; IEEE 17th International Conference on Smart City; IEEE 5th International Conference on Data Science and Systems, pp. 154-161, doi: 10.1109/HPCC/SmartCity/DSS.2019.00036.

Ali Gunawan, "Selection of Open Source Database Management for System Development Using Analytic Hierarchy Process Method in PT. XYZ", 2020 International Conference on Information Management and Technology (ICIMTech), Aug. 13-14, 2020.

Yoonjoo Kim et al., "Respiratory sound classification for crackles, wheezes, and rhonchi in the clinical field using deep learning", Scientific Reports, (2021) 11:17186, Aug. 25, 2021, https://doi.org/10.1038/s41598-021-96724-7.

Nourelhuda Mohamed et al., "Heart and Lung Sound Measurement Using an Esophageal Stethoscope with Adaptive Noise Cancellation", Sensors 2021, 21, 6757. Oct. 12, 2021, https://doi.org/10.3390/s21206757.

Jean-Michel Arnal et al., "Monitoring Systems in Home Ventilation", J. Clin. Med. 2023, 12, 2163. Mar. 10, 2023, https://doi.org/10.3390/jcm12062163.

* cited by examiner

FIG. 2

ELECTROCARDIOGRAM

PRESSURE

RESPIRATION SOUND

FLOW RATE

HEART SOUND

VOLUME

FIG. 6

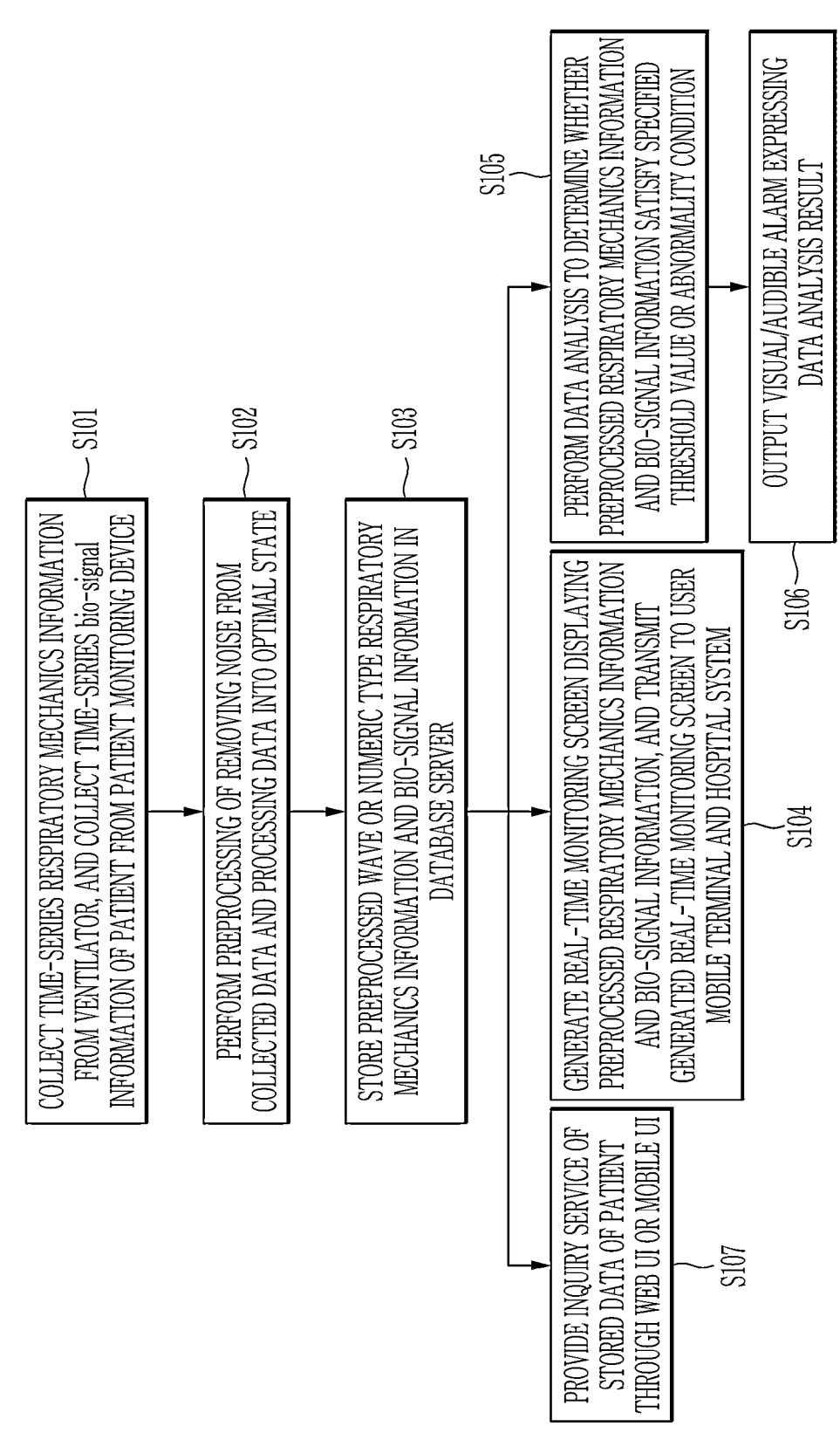

S101
COLLECT TIME-SERIES RESPIRATORY MECHANICS INFORMATION FROM VENTILATOR, AND COLLECT TIME-SERIES bio-signal INFORMATION OF PATIENT FROM PATIENT MONITORING DEVICE S102
PERFORM PREPROCESSING OF REMOVING NOISE FROM COLLECTED DATA AND PROCESSING DATA INTO OPTIMAL STATE S103
STORE PREPROCESSED WAVE OR NUMERIC TYPE RESPIRATORY MECHANICS INFORMATION AND BIO-SIGNAL INFORMATION IN DATABASE SERVER S104
GENERATE REAL-TIME MONITORING SCREEN DISPLAYING PREPROCESSED RESPIRATORY MECHANICS INFORMATION AND BIO-SIGNAL INFORMATION, AND TRANSMIT GENERATED REAL-TIME MONITORING SCREEN TO USER MOBILE TERMINAL AND HOSPITAL SYSTEM S105
PERFORM DATA ANALYSIS TO DETERMINE WHETHER PREPROCESSED RESPIRATORY MECHANICS INFORMATION AND BIO-SIGNAL INFORMATION SATISFY SPECIFIED THRESHOLD VALUE OR ABNORMALITY CONDITION

S106
OUTPUT VISUAL/AUDIBLE ALARM EXPRESSING DATA ANALYSIS RESULT

S107
PROVIDE INQUIRY SERVICE OF STORED DATA OF PATIENT THROUGH WEB UI OR MOBILE UI

FIG. 7

GENERATE, AS LEARNING DATA, PAIR DATA INCLUDING
MEASURED RESPIRATORY MECHANICS INFORMATION,
PERSONAL STATE INFORMATION OF PATIENT,
AND MEDICAL PERSONNEL OPINION INFORMATION — S201

USE LEARNING DATA TO TRAIN ABNORMAL SIGNAL
DETECTION MODEL DETERMINING NORMAL SIGNAL OR
ABNORMAL SIGNAL FROM INPUT DATA AND CLASSIFYING
ABNORMAL SIGNAL OCCURRENCE CAUSE TYPE — S202

FIG. 13

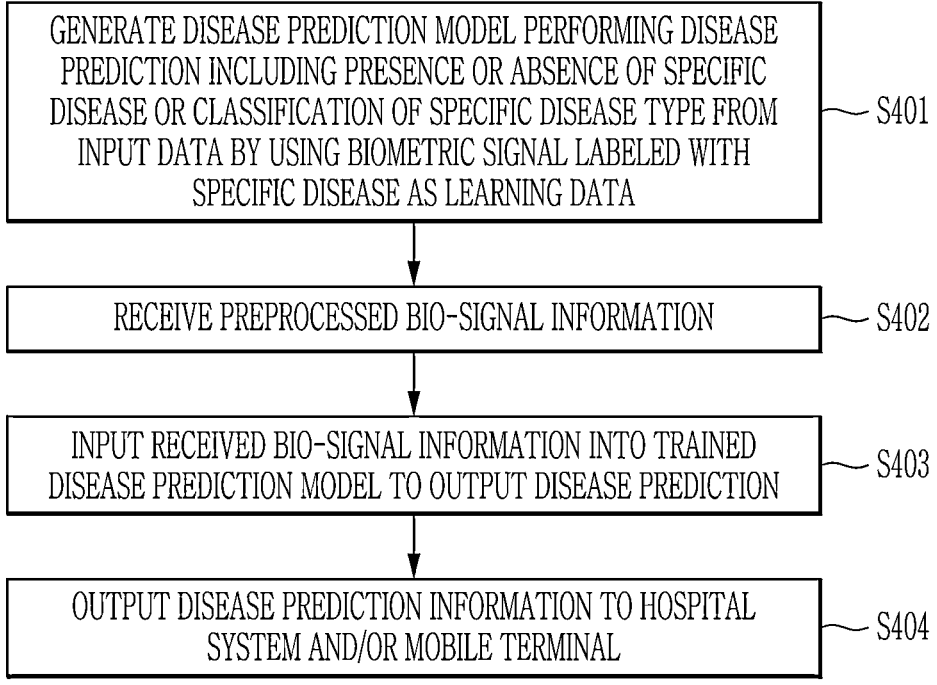

GENERATE DISEASE PREDICTION MODEL PERFORMING DISEASE PREDICTION INCLUDING PRESENCE OR ABSENCE OF SPECIFIC DISEASE OR CLASSIFICATION OF SPECIFIC DISEASE TYPE FROM INPUT DATA BY USING BIOMETRIC SIGNAL LABELED WITH SPECIFIC DISEASE AS LEARNING DATA — S401

RECEIVE PREPROCESSED BIO-SIGNAL INFORMATION — S402

INPUT RECEIVED BIO-SIGNAL INFORMATION INTO TRAINED DISEASE PREDICTION MODEL TO OUTPUT DISEASE PREDICTION — S403

OUTPUT DISEASE PREDICTION INFORMATION TO HOSPITAL SYSTEM AND/OR MOBILE TERMINAL — S404

CONVERT ONE-DIMENSIONAL SOUND TYPE RESPIRATION SOUND MEASUREMENT SIGNAL TO TWO-DIMENSIONAL (2D) IMAGE — S501

PERFORM PREPROCESSING OF REMOVING HEART SOUND AND EXTERNAL NOISE FROM 2D IMAGE — S502

TRAIN DISEASE PREDICTION MODEL CLASSIFYING PRESENCE OR ABSENCE OF RESPIRATION DISEASE AND/OR TYPE OF RESPIRATORY DISEASE BY USING PREPROCESSED 2D IMAGE AS LEARNING DATA — S503

METHOD, SERVER, AND SYSTEM INTELLIGENT VENTILATOR MONITORING USING NON-CONTACT AND NON-FACE-TO-FACE

CROSS-REFERENCE TO RELATED APPLICATION

This application claims priority to and the benefit of Korean Patent Application No. 10-2022-0172338 filed in the Korean Intellectual Property Office on Dec. 12, 2022, and Korean Patent Application No. 10-2023-0020781 filed in the Korean Intellectual Property Office on Feb. 16, 2023, the entire contents of which are incorporated herein by reference.

BACKGROUND OF THE INVENTION

(a) Field of the Invention

The present disclosure relates to method, server, and system intelligent ventilator monitoring using non-contact and non-face-to-face.

(b) Description of the Related Art

A ventilator may supply a respiratory gas including high oxygen tension to a patient at appropriate pressure, volume, and frequency to thus help or regulate respiration of the patient and induce relaxation of his/her respiratory muscle. The ventilator may be essential equipment for a patient with moderate hypoxia as well as a patient with severe hypoxia among the patients with hypoxia. In particular, the ventilator may be essential to treat a patient with a respiratory failure who has hypoxemia or hypercapnia caused by inflammation of a lung parenchyma or deterioration of the respiratory muscle.

A mechanical ventilator may include a ventilator including a compressor that generates a pressure required for the respiration of each patient, and valves and cannula delivering the respiratory gas to the patient.

A mechanical ventilator market is growing rapidly due to an outbreak of novel corona virus infection (COVID-19) and an increase in the number of patients with chronic obstructive pulmonary disease (COPD). Starting with COVID-19, China's ventilator imports showed a rapid increase of 41.1% (or approximately $240 million) in the first half of 2020 compared to the same period of the last year. A worldwide average annual growth rate of the mechanical ventilator market is approximately 4.8%, and the market is expected to grow to $4.22 billion in 2030.

In particular, a non-invasive home care respiratory therapy device market may be a rapidly growing new market. Its average annual growth rate is 11.8%, and this market is expected to grow to approximately 9 trillion won in 2025 with global giants expected to competitively dominate the market.

In addition, in accordance with the fourth industrial revolution, there is an emerging need for automatic patient monitoring and prognosis prediction based on various structured/unstructured data, and related hardware/software technologies are also achieving remarkable growth.

A conventional ventilator may be operated in such a way that medical personnel (e.g., a doctor or a nurse) check a state of each patient through a state monitor and an alarm to stably maintain a respiratory cycle of the patient. That is, conventional ventilator monitoring is performed in such a way that respiratory mechanics (i.e., pressure, frequency, and volume) of the patient are shown to the medical personnel (e.g., the doctor or the nurse) in a face-to-face manner through a monitor attached to each machine, and the medical personnel check the monitor and then make direct contact with the patient to thus stably maintain the respiration of the patient.

However, to manage each of the plurality of patients through individual ventilator monitoring equipment may have a physical limitation in providing, by the medical personnel, the patient with a nursing care or a rapid management in emergency.

In addition, there is a risk that the medical personnel are exposed to an infectious bacteria when managing a patient infected with airborne strains such as COVID-19, MERS, SARS, pulmonary tuberculosis, disseminated chickenpox, or the like in the direct contact and face-to-face manner.

In addition, the alarm may be generated from the ventilator monitor of a patient who has been quarantined due to this possibility of infection transmission to thus require direct ventilator regulation by the medical personnel. In this case, the quarantine may delay recognition of the ventilator alarm by the medical personnel, or the respiratory regulation may be delayed while the medical personnel are wearing protective clothing, which may result in unfortunate outcomes for the patient.

In addition, continuous/continual management of the patient with respiratory disease in an analog manner requires the establishment of a many-to-one relationship between nursing personnel and the patient. However, this relationship is impossible due to a current medical environment. In addition, in a case of a home ventilator, it may be very difficult to secure manpower to detect a signal and regulate a respiration volume for 24 hours or more.

In addition, the conventional ventilator may use an abnormal signal notification method in which normal and abnormal states are determined by setting thresholds and ranges of several parameters such as oxygen saturation ($SpO_2$), a maximum inspiratory pressure (PI), a pulse rate (PR), a body temperature, a diastolic blood pressure, a respiratory rate, a tidal volume, the respiration volume per minute, plateau pressure, and lung compliance, and the alarm is output using the alarm and a screen message when determining the abnormal state.

However, the above-mentioned parameter-based abnormal signal alarm which shows only a momentary abnormal signal rather than continuous values may not correspond to values changed based on the situation and surrounding condition of the patient, thus have a limitation in showing an overall flow. Therefore, it is difficult for the conventional ventilator to precisely detect the abnormal signal tailored to each patient. In addition, when monitoring a recovery state of the patient, it is difficult for the conventional ventilator to determine various features of a respiratory signal, which makes it difficult to predict the prognosis.

SUMMARY OF THE INVENTION

The present disclosure attempts to provide method, device, and system for integrated monitoring and control of a ventilator installed in a home or a hospital using non-contact and non-face-to-face.

The present disclosure attempts to provide a following method, an integrated monitoring server and an integrated monitoring system, the method of receiving ventilation data in real time from a ventilator of a patient that is installed in a remote location, receiving a bio-signal of the patient in real time from a patient monitoring device including various bio-signal measurement sensors, performing preprocessing of removing a noise from the real-time received ventilation data and bio-signal and processing the same into a specified format, outputting a monitoring screen displaying the preprocessed ventilation data and bio-signal to mobile terminals of medical personnel and a hospital system, generating a visual/audible alarm when an abnormal symptom is detected in the preprocessed ventilation data or bio-signal to transmit the same to the mobile terminals of the medical personnel and the hospital system, and performing a remote control to restore normal respiration of the patient.

The present disclosure attempts to provide a following method, an integrated monitoring server and an integrated monitoring system, the method of performing data analysis to classify an abnormal signal occurrence cause type or/and a disease type from input data by using an artificial intelligence model trained by using respiratory mechanics information or/and biometric signal as learning data, and transmitting data analysis information to the hospital system or the mobile terminals of the medical personnel.

According to an embodiment, provided is a method of operating an integrated monitoring server operated by at least one processor, the method including: receiving waveform-type respiratory mechanics information in real time from a ventilator of a patient that is installed at a remote location, and transmitting the real-time received waveform-type respiratory mechanics information to a hospital system connected to the server through a dedicated line or mobile terminals of medical personnel connected to the server through an internet.

Between the receiving and the transmitting, the method may further include performing preprocessing of removing a noise from the real-time received respiratory mechanics information and processing the information into a specified format, wherein in the transmitting, the preprocessed real-time received respiratory mechanics information is transmitted.

In the receiving, various biometric signals of the patient may be further received from a patient monitoring device installed at the remote location and preprocessed, and in the transmitting, an integrated monitoring screen displaying the preprocessed respiratory mechanics information and biometric signal may be generated, and the integrated monitoring screen may be transmitted.

In the preprocessing, an external noise may be measured, and the noise may be removed from the real-time received respiratory mechanics information by using the measured external noise.

In the preprocessing, a threshold value may be specified and a signal of the threshold value or less may be removed, after the time-series information is transformed to another domain.

In the preprocessing, a noise component may be removed using machine learning.

In the preprocessing, the respiratory mechanics information may be converted to a health level 7 (HL7) protocol which is a form usable by the hospital system.

After the preprocessing, the method may further include: performing data analysis to determine whether the preprocessed data satisfies the specified threshold value or abnormal symptom condition; and transmitting a visual or audible alarm expressing a data analysis result to the mobile terminals of the medical personnel or the hospital system.

After the transmitting, the method may further include providing an inquiry service for stored data of the patient through a web user interface or a mobile user interface.

After the real-time receiving, the method may further include: determining whether an abnormal signal occurs in the received respiratory mechanics information and classifying an abnormal signal occurrence cause type by using an abnormal signal detection model trained to classify the presence or absence of the abnormal signal or the abnormal signal occurrence cause type from input data; and transmitting analysis information including the presence or absence of the abnormal signal or the abnormal signal occurrence cause type to the hospital system or the mobile terminal.

Before the classifying, the method may further include: generating, as learning data, pair data including measured respiratory mechanics information, personal state information of the patient, and medical personnel opinion information; and generating the abnormal signal detection model by using the generated learning data.

In the transmitting, when the abnormal signal is determined to occur, and the determined abnormal signal occurrence cause type is determined to require an emergency alarm, an emergency warning message and an audible alarm notifying the abnormal signal occurrence and the abnormal signal occurrence cause type may be generated and transmitted.

After the real-time receiving, the method, in which in the real-time receiving, a biometric signal including at least one of the respiration sound, heart sound, and electrocardiogram of the patient is further received from a patient monitoring device installed at the remote location, may further include: classifying the presence or absence of specific disease or a disease type of the patient from the received biometric signal by using a disease prediction model trained to classify the presence or absence of the specific disease or the disease type from input data; and transmitting analysis information including the presence or absence of the specific disease or the disease type of the patient to the hospital system or the mobile terminal.

Before the classifying, the method may further include: generating the biometric signal labeled with the specific disease or the biometric signals labeled with various diseases as learning data; and generating the disease prediction model by using the generated learning data.

In the generating of the disease prediction model, the disease prediction model classifying the presence or absence of respiration disease and/or a respiratory disease type may be trained by converting a one-dimensional sound type respiration sound measurement signal to a two-dimensional (2D) image, performing preprocessing of removing the noise from the converted 2D image, and using the preprocessed 2D image as the learning data.

In the generating of the disease prediction model, a multi-channel respiration sound measurement signal may be used as the learning data.

After the real-time receiving, the method, in which in the real-time receiving, a biometric signal including at least one of the respiration sound, heart sound, and electrocardiogram of the patient is further received from a patient monitoring device installed at the remote location, may further include: classifying an abnormal signal occurrence cause type or a specific disease type from the received respiratory mechanics information and biometric signal by using an artificial intelligence model trained to classify the abnormal signal occurrence cause type or the specific disease type from input data; and transmitting analysis information including the classified abnormal signal occurrence cause type and specific disease type to the hospital system or the mobile terminal.

According to another embodiment, an integrated monitoring server includes: a data collection unit receiving waveform-type respiratory mechanics information from a ventilator of a patient that is installed at a remote location, and receiving various biometric signals measured in real time from a patient monitoring device installed at the remote location; and a data provision unit transmitting the real-time received waveform-type respiratory mechanics information and various biometric signals to a hospital system connected thereto through a dedicated line or mobile terminals of medical personnel connected thereto through an internet.

The server may further include a data processing unit performing preprocessing of removing a noise and processing the real-time received respiratory mechanics information and biometric signal into a specified format, wherein the data provision unit transmits the preprocessed real-time received respiratory mechanics information and biometric signal.

The data processing unit may further perform preprocessing of converting the respiratory mechanics information to a health level 7 (HL7) protocol which is a form usable by the hospital system, and output the respiratory mechanics information converted to the H7 protocol in real time to the data provision unit.

The server may further include a data analysis unit performing data analysis to determine whether the preprocessed data satisfies the specified threshold value or abnormal symptom condition, wherein the data provision unit transmits a visual or audible alarm expressing a data analysis result based on an instruction of the data analysis unit to the mobile terminals of the medical personnel or the hospital system.

The data provision unit may provide an inquiry service for stored data of the patient through a web user interface or a mobile user interface.

According to still another embodiment, an integrated monitoring system includes: a home ventilator installed at a remote location, measuring respiratory mechanics information of a patient, and transmitting the measured respiratory mechanics information in real time; a hospital ventilator installed in a hospital, measuring the respiratory mechanics information of the patient, and transmitting the measured respiratory mechanics information in real time; and an integrated monitoring server connected to the home ventilator through a network and receiving the waveform-type respiratory mechanics information, connected to the hospital ventilator through a dedicated line and receiving the waveform-type respiratory mechanics information, and transmitting the real-time respiratory mechanics information to a server device of the hospital or mobile terminals of medical personnel connected thereto through an internet.

The system may further include a patient monitoring device installed at the remote location to measure various bio-signals of the patient, wherein the integrated monitoring server receives various biometric signals of the patient together with the waveform-type respiratory mechanics information, and transmits an integrated monitoring screen displaying the respiratory mechanics information and the various biometric signals.

The integrated monitoring server may perform preprocessing of removing a noise and processing the real-time received respiratory mechanics information and biometric signal into a specified format, and transmit the preprocessed real-time received respiratory mechanics information and biometric signal.

The integrated monitoring server may perform data analysis to determine whether the preprocessed data satisfies the specified threshold value or abnormal symptom condition, and transmit a visual or audible alarm expressing a data analysis result to the mobile terminals of the medical personnel or the hospital system.

According to yet another embodiment, an integrated monitoring server includes: a data collection unit receiving waveform-type respiratory mechanics information from a ventilator of a patient that is installed at a remote location or various biometric signals measured in real time from a patient monitoring device installed at the remote location; a data analysis unit classifying an abnormal signal occurrence cause type or a specific disease type by using an artificial intelligence model trained to classify the abnormal signal occurrence cause type or the specific disease type from input data to input the respiratory mechanics information or the biometric signal, received by the data collection unit, to the artificial intelligence model; and a data provision unit transmitting analysis information of the data analysis unit to a hospital system or mobile terminals of medical personnel.

The artificial intelligence model may include a disease prediction model classifying the presence or absence of respiration disease or a respiratory disease type, and the data analysis unit may train the disease prediction model by converting a one-dimensional sound type respiration sound measurement signal to a two-dimensional (2D) image, performing preprocessing of removing a noise from the converted 2D image, and using the preprocessed 2D image as learning data.

The artificial intelligence model may include a disease prediction model trained to classify the presence or absence of specific disease or the disease type from the input data, and the data analysis unit may input the biometric signal including at least one of the respiration sound, heart sound, and electrocardiogram of the patient, received by the data collection unit, into the disease prediction model to classify the presence or absence of the specific disease or disease type of the patient.

The artificial intelligence model may include an abnormal signal detection model trained to classify the presence or absence of an abnormal signal or the abnormal signal occurrence cause type from the input data, and the data analysis unit may input the respiratory mechanics information received by the data collection unit into the abnormal signal detection model to classify the presence or absence of the abnormal signal or the abnormal signal occurrence cause type.

The data analysis unit may generate, as learning data, pair data including the measured respiratory mechanics information, personal state information of the patient, and medical personnel opinion information, and generate the abnormal signal detection model by using the generated learning data.

The abnormal signal detection model may classify the abnormal signal occurrence cause type as one of a ventilator cause type, an airway cause type, and an abnormal patient respiration state cause type from the input data.

The abnormal signal detection model may output the abnormal signal occurrence cause type as probability information for each of a ventilator cause type, an airway cause type, and an abnormal patient respiration state cause type.

As set forth above, according to the present disclosure, it is possible to collect in real time the data including the respiratory mechanics information measured from the ventilator of the patient that is installed in the remote location, and the bio-signals (e.g., electrocardiogram, heart sound, and respiration sound) of the patient that are measured through the various sensors, and preprocess and transmit the same in real time to the mobile terminals of the medical personnel and the hospital system, thus performing the integrated monitoring by the central center using the non-face-to-face, and controlling the ventilator of each patient by using the non-contact and non-face-to-face immediately after the alarm is recognized.

In addition, according to the present disclosure, it is possible to perform the integrated monitoring and control of the vantilizations and bio-signals of the plurality of patients, thus maximizing the efficiency of treatment and monitoring costs, and reducing the risk of medium/high risk infections to the medical personnel through the patient management manner using the non-contact and non-face-to-face. In addition, it is possible to consider the present disclosure to expand to home ventilator monitoring equipment, which is increasingly used in facilities (e.g., homes, silver towns, or nursing homes) other than the hospitals due to the aging society.

In addition, according to the present disclosure, it is possible to manage the mechanical respiration in the hospitals and homes through the cloud service with enhanced information security.

In addition, the present disclosure may have a very high impact in enabling the establishment of the precise and systematic food inspection and management system based on the image analysis result, and capable of being directly applied to the various industrial and medical fields in addition to the patient respiration management.

In addition, according to the present disclosure, it is possible to predict the abnormal state of the ventilator of the patient and the presence or absence of the patient disease based on the respiratory mechanics information and biometric signal measured by the ventilator of the patient, and provide the result to the medical personnel, thus enabling the efficient treatment/management of the patient even in the remote location.

BRIEF DESCRIPTION OF THE DRAWINGS

FIG. 2 is a block diagram showing a detailed configuration of an integrated monitoring server according to an embodiment.

FIG. 6 is a flowchart showing an operation of the integrated monitoring server according to an embodiment.

FIG. 7 is a conceptual diagram showing ventilator data analysis using artificial intelligence technology according to an embodiment.

FIG. 13 is a flowchart explaining a data analysis procedure using the disease prediction model according to an embodiment.

DETAILED DESCRIPTION OF THE EMBODIMENTS

Figure 1:
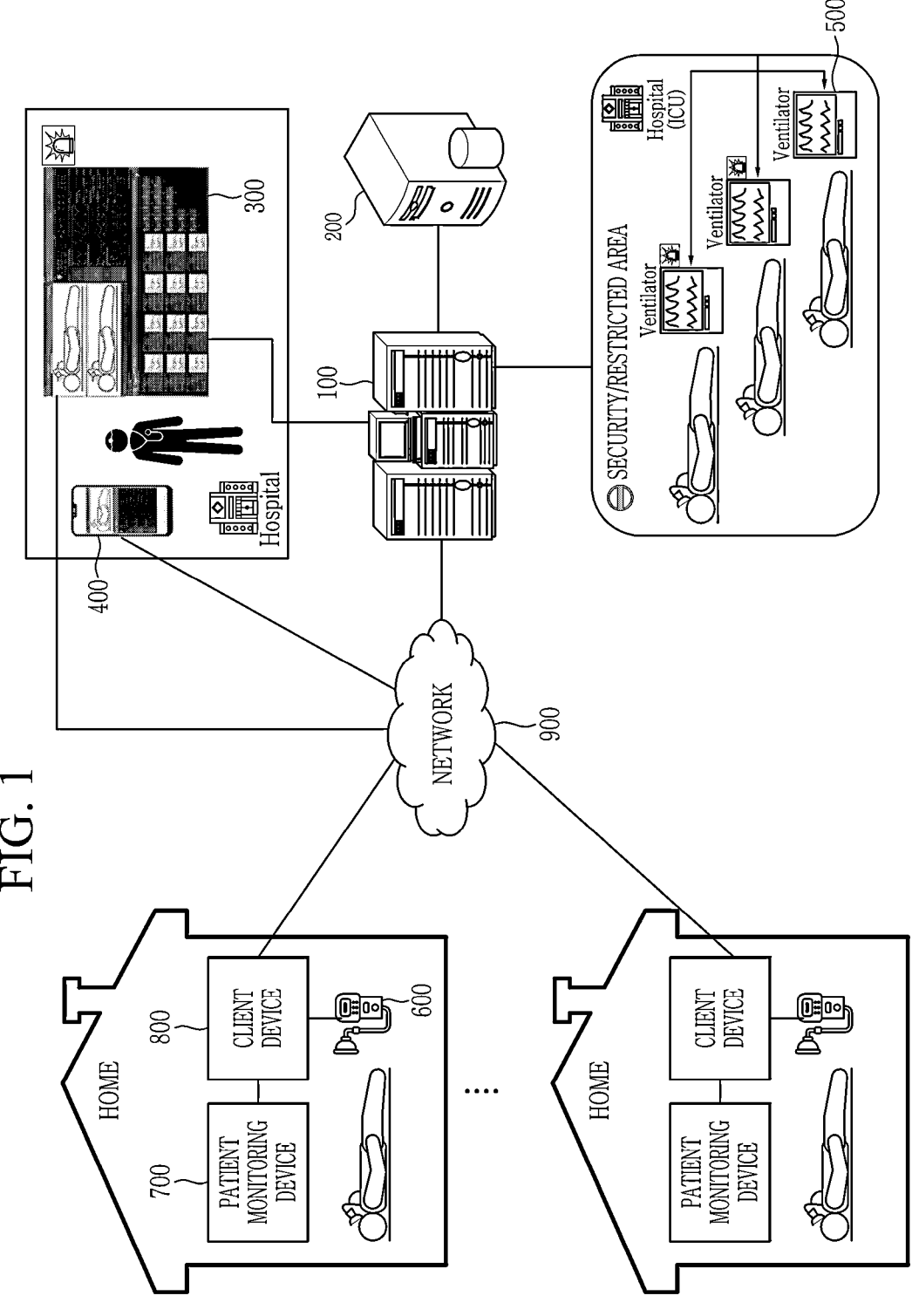
FIG. 1 is a configuration diagram of an intelligent ventilator monitoring system using non-contact and non-face-to-face according to an embodiment.

Hereinafter, embodiments of the present disclosure are described in detail with reference to the accompanying drawings so that those skilled in the art to which the present disclosure pertains may easily practice the present disclosure. However, the present disclosure may be modified in various different forms, and is not limited to the embodiments provided in the specification. In addition, in the drawings, portions unrelated to the description are omitted to clearly describe the present disclosure, and similar portions are denoted by similar reference numerals throughout the specification.

In the description, reference numerals and names are added for convenience of explanation, and devices are not necessarily limited by the reference numerals or the names.

Unless explicitly described to the contrary, "including" any components will be understood to imply the inclusion of other components rather than the exclusion of any other components.

In addition, the terms "part", "module", and the like, described in the present disclosure mean a unit of processing at least one function or operation and may be implemented by hardware or software or a combination of hardware and software.

The devices described in the present disclosure may include hardware including at least one processor, memory device, communication device, or the like, and store a program executed in combination with the hardware in a specified location. The hardware may have the configuration and capability to perform a method of the present disclosure. The program may include instructions for implementing an operation method of the present disclosure described with reference to the drawings, and execute the present disclosure in combination with the hardware such as the processor and the memory device.

In the specification, "transmission" or "provision" may include not only direct transmission or provision, but also indirect transmission or provision through another device or using a bypass path.

A term of a singular number in the specification may be interpreted as the singular number or its plural number unless explicitly expressed such as "one" or "single."

In the specification, the same reference numbers refer to the same elements regardless of the drawings, and "and/or" includes each and every combination of one or more of the mentioned elements.

Terms including ordinal numbers such as "first", "second", and the like, may be used to describe various components. However, these components are not limited by these terms. These terms are used only to distinguish one component from another component. For example, a first component may be named a second component and the second component may also be similarly named the first component, without departing from the scope of the present disclosure.

In a flowchart described with reference to the drawings, an order of operations may be changed, several operations may be merged with each other, a certain operation may be divided, and a certain operation may not be performed.

In the specification, an artificial intelligence model (or AI model) may be a machine learning model learning at least one task, and may be implemented as a computer program executed by the processor. The task that the artificial intelligence model learns may refer to a task to be solved through machine learning or a task to be performed through machine learning. The artificial intelligence model may be implemented as the computer program executed by the computing device, downloaded through a network, or sold in a product form. Alternatively, the artificial intelligence model may link with various devices through the network.

FIG. 1 is a configuration diagram of an intelligent ventilator monitoring system using non-contact and non-face-to-face according to an embodiment.

Referring to FIG. 1, the intelligent ventilator monitoring system using non-contact and non-face-to-face may include an integrated monitoring (or ventilator central monitoring system, VCMS) server 100, a database server 200, a hospital system 300, a mobile terminal 400, a hospital ventilator 500, a home ventilator 600, a patient monitoring device 700, and a client device 800.

The integrated monitoring server 100 may allow a central monitoring console operator to monitor biometric information of each patient in real time, and control a patient with an abnormal body parameter for the patient to be immediately treated.

The integrated monitoring server 100 may collect respiratory mechanics information from the plurality of hospital ventilators 500 installed in a hospital and the home ventilator 600 installed at a remote location, and collect various biometric signals from the patient monitoring device 700 installed at the remote location, thus generating a real-time integrated monitoring screen displaying the collected information, and outputting the generated real-time integrated monitoring screen to the hospital system 300 and the mobile terminals 400 of medical personnel.

The integrated monitoring server 100 may support an action tailored to the patient, either face-to-face or remotely, by collecting the respiratory mechanics information and the biometric signal through the real-time monitoring in a wired/wireless manner, monitoring and storing the body parameter of the patient to be tailored to a client, i.e., the patient, based on the collected information, and providing a visual/audible alarm signal when an abnormal symptom occurs in the input body parameter of the patient.

The integrated monitoring server 100 may check the respiration pressure, respiration flow, and respiration volume of the patient in real time, display a waveform, and display the visual/audible alarm at a critical point or more.

The database server 200 may receive the respiratory mechanics information and the biometric signal from integrated monitoring server 100 to map and store the same for each patient. The stored information may be inquired by the mobile terminal 400 or the hospital system 300. Here, the stored information may be processed and stored in a form that the information may be inquired.

The hospital system 300 may output the integrated monitoring screen received from the integrated monitoring server 100. The hospital system 300 may be an electronic medical record (EMR) system, a central monitoring system (CMS), or the like.

The mobile terminal 400 may output the integrated monitoring screen received from the integrated monitoring server 100.

The mobile terminal 400 may be a personal electronic communication device (e.g., smartphone) of the medical personnel permitted to access to or communicate with the integrated monitoring server 100 through a cloud service. The mobile terminal 400 may be installed with an application to provide the dedicated cloud service for the embodiments of the present disclosure, and may be checked inside/outside the hospital. Therefore, the integrated monitoring server 100 may transmit integrated monitoring information/analysis/alarm information to the mobile terminal 400 through the secure cloud service, thus allowing the medical personnel to check a patient state in real time.

When the abnormal symptoms occurs, the hospital system 300 and the mobile terminal 400 may receive the visual/audible alarm notifying the occurrence of the abnormal symptom from the integrated monitoring server 100 and output the same.

The hospital ventilator 500 and the home ventilator 600 may measure the respiratory mechanics information of the patient, and transmit the measured respiratory mechanics information to the integrated monitoring server 100 in real time.

The hospital ventilator 500 or the home ventilator 600 may be equipment used to maintain adequate emissions of oxygen ($O_2$) and carbon dioxide ($CO_2$) to maintain gas exchange at a level for supplying sufficient oxygen to an important organ of the patient.

The hospital ventilator 500 or the home ventilator 600 may prevent lung damage, oxygen toxicity, structural damage to an airway, or the like, thus supporting the patient until a primary injury is replaced, and maintaining the patient in an optimal state for early recovery of his/her normal respiration.

The hospital ventilator 500 or the home ventilator 600 may include an intake regulation valve for mainly regulating the flow rate and hydraulic pressure of a mixed gas provided to the patient and supplying the same to a patient lung, a positive end-expiratory pressure valve for discharging an exhaust gas to the outside by regulating the flow rate and hydraulic pressure of the exhaust gas discharged from the patient lung, and a control module generating a driving signal for patient respiration based on the biometric information on a structural property of a patient alveoli and providing the generated structural signal to the intake regulation valve and the positive end-expiratory pressure valve.

The patient monitoring device 700 may be installed at the remote location, that is, at home, and may include various sensors measuring bio-signals of the patient. The various sensors may include a heart rate sensor and a respiration sound (or lung sound) sensor.

The heart rate sensor may include at least one of an electrocardiograph (ECG/EKG) measurement sensor, a photoelectric plethysmographic measurement sensor, a sphyg-momanometer measurement sensor, and an echocardiography measurement sensor.

The electrocardiograph measurement sensor may record and output that when a heart myocardium is active, an electrical excitement is generated and an action potential is generated, and a corresponding energy is transferred through a body surface as a waveform by a current. The heart action potential may have a small potential difference of 1 mV or less, and require a very sensitive galvanometer. Representatively, the electrocardiograph measurement sensor may include a current electrocardiograph based on a saiten galvanometer (which is a type of string galvanometer) using a quartz or platinum wire, may have very high measurement accuracy, and may be mainly used for a heart test, a monitoring device during a surgery, critical patient monitoring, or the like.

The photoelectric plethysmographic measurement sensor may measure a pulse wave by emitting infrared light, red light, or a green wavelength around 550 nm, to a living organism, and measuring information reflected or attenuated by hemoglobin in a blood vessel by using a photodiode or a phototransistor. Oxidized hemoglobin may exist in an arterial blood and have a property of absorbing incident light. The photoelectric plethysmographic measurement sensor may measure a change in a blood flow rate (mainly, a change in a blood vessel volume) in a time series based on a heart pulsation. An example of the photoelectric plethysmographic measurement sensor may include a reflective pulse wave sensor.

The sphygmomanometer measurement sensor may measure a change in a blood vessel pressure based on the heart pulsation. The sphygmomanometer measurement sensor may listen to a sound (i.e., Korotkoff sound), which is generated by wrapping an upper arm to compress an artery, then temporarily blocking the blood flow, and then gradually releasing the compression, with a stethoscope, measure a blood pressure unit of mmHg when the sound is generated, and mainly use an electronic measurement and recording method. An example of the sphygmomanometer measurement sensor may include a mercury sphygmomanometer sensor or an electronic sphygmomanometer sensor.

The echocardiography measurement sensor may measure a sound generated based on the heart pulsation. The echocardiography measurement sensor may be used mainly together with the electrocardiogram to perform the measurement and improve an accuracy of heart disease measurement.

The respiration sound (or lung sound) measurement sensor may include at least one of a condenser microphone sensor, a piezo film sensor, and a piezo disc sensor.

The microphone sensor may be a device converting an acoustic signal to an electrical signal. The microphone sensors may be classified into carbon, crystal, and magnetic microphones based on their materials, and classified into a dynamic microphone using an induced electromotive force of a magnetic field and a condenser microphone using a change in a capacitance due to vibration of a membrane, based on an operation principle of an acoustic sensor. In particular, the condenser microphone may be small-sized and mass-produced at a lower cost through a micro-electro-mechanical system (MEMS) process.

The piezo film sensor may apply a pressure by using power of a sound wave to generate a voltage (piezoelectricity) or apply the pressure to deform the voltage (or generate reverse piezoelectricity). A piezoelectric material may mainly include zinc oxide (ZnO), lead zirconate titanate (PZT), aluminum nitride (AlN), or the like, and PZT may be mainly used because of its very high piezoelectric performance. The piezo film sensor may have a thickness of approximately several μm, which allows a device with miniaturization, integration, high precision, and low power consumption.

The piezo disc sensor may convert the sound wave to the electrical signal based on the same principle as the piezo film sensor. The piezoelectric material may use ceramic-based barium titanate ($BaTiO_3$), lead zirconate titanate (PZT), or the like, and have a thickness of several millimeters. The piezo disk sensor may have a greater thickness than the piezo film sensor.

The client device 800 may be installed in the remote location, that is, at home, may be connected to the home ventilator 600 and the patient monitoring device 700 in the wired or wireless manner, and may serve as a communication device collecting and transmitting the respiratory mechanics information and the biometric signal.

The client device 800 may be included in each of the home ventilator 600 the patient monitoring device 700.

Here, the client device 800 may generate a patient monitoring signal including the respiratory mechanics information and the biometric signal and including a patient identifier and a device identifier, and transmit the same to the integrated monitoring server 100.

The integrated monitoring server 100 may be physically directly connected with the database server 200.

The integrated monitoring server 100 may communicate with the hospital system 300 and the hospital ventilator 500 through a dedicated line (e.g., hospital internal network or dedicated network), and perform the communicate via a transmission control protocol/internet protocol (TCP/IP).

The integrated monitoring server 100 may communicate with the mobile terminal 400 and the client device 800 through a network 900.

According to an embodiment, the integrated monitoring server 100 may implement the above-described integrated monitoring service through a dedicated server resource.

According to another embodiment, the integrated monitoring server 100 may implement the above-described integrated monitoring service through the cloud service provided by a third-party provider based on an internet connection. Here, the cloud service may use various known cloud services such as Amazon web service (AWS).

Figure 2:
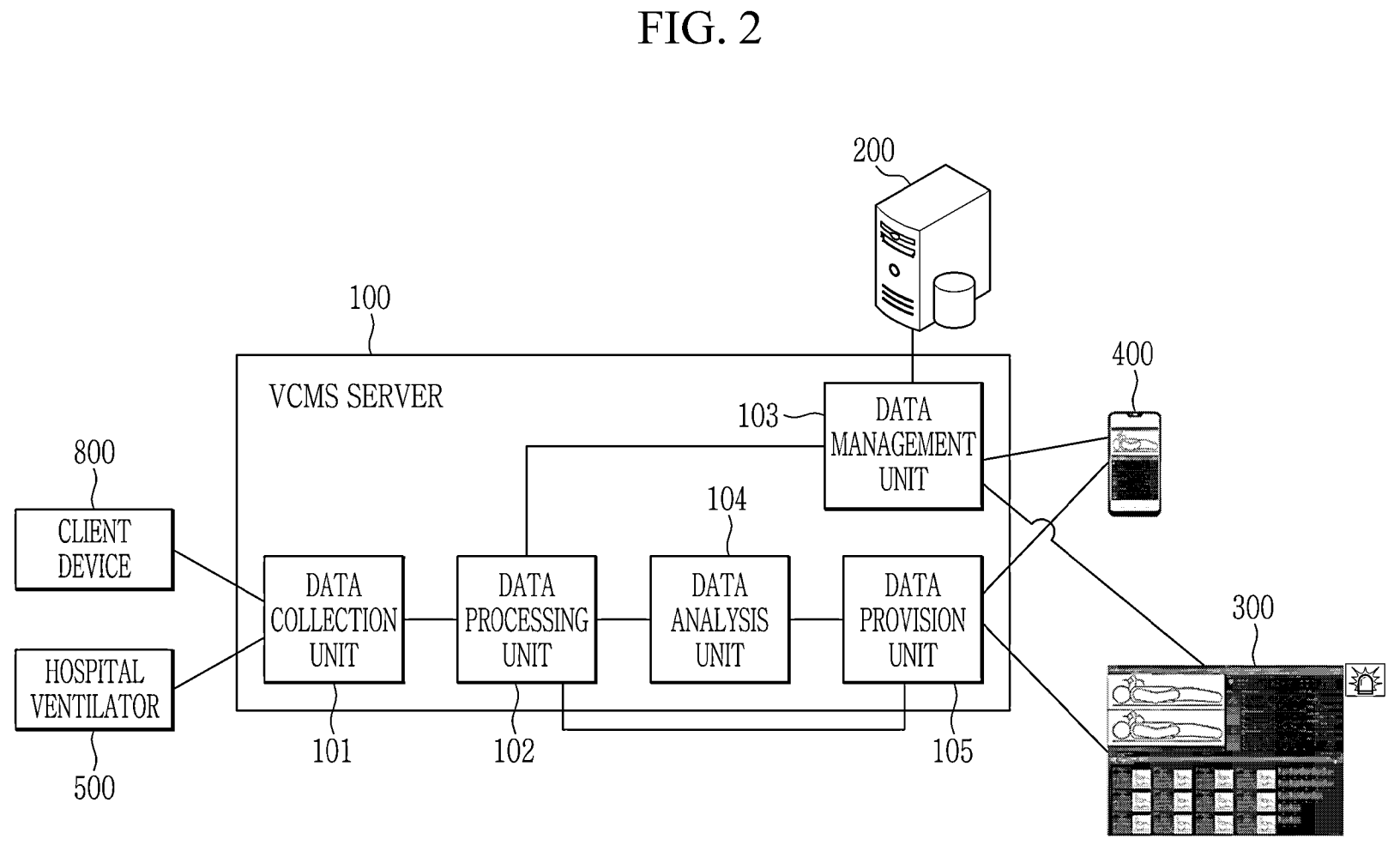
Figure 3:
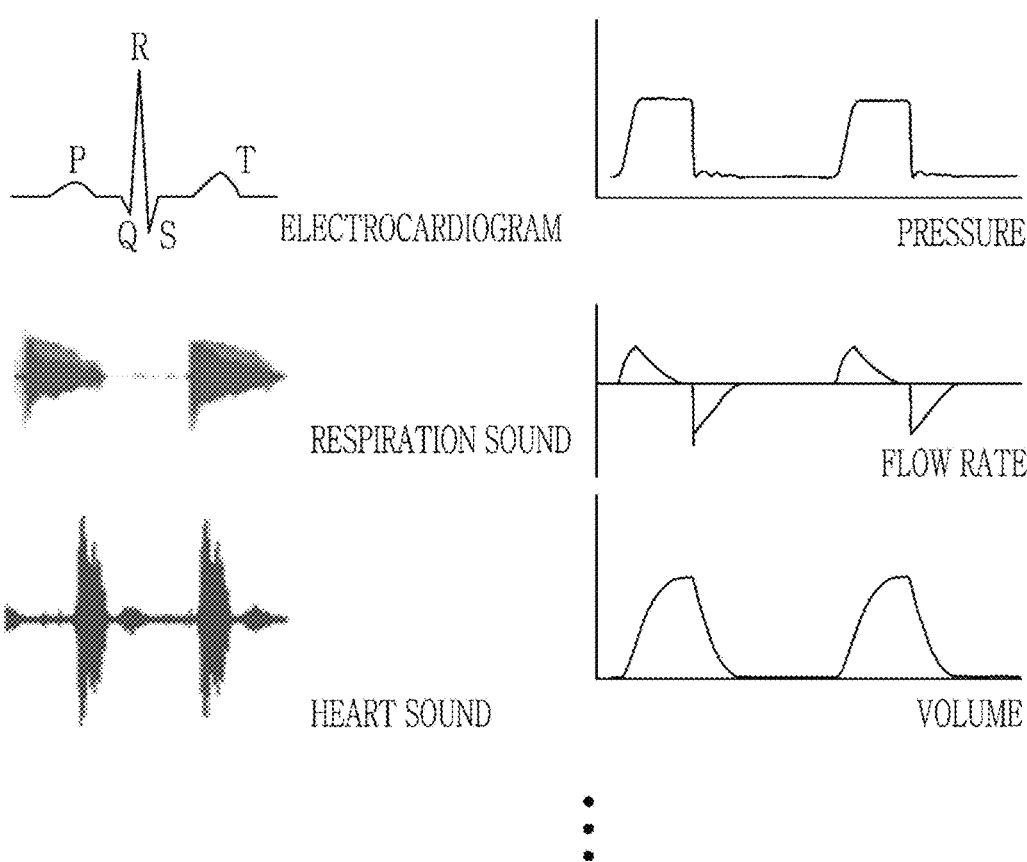
FIG. 3 is an example diagram showing a form of collected data according to an embodiment.
Figure 4:
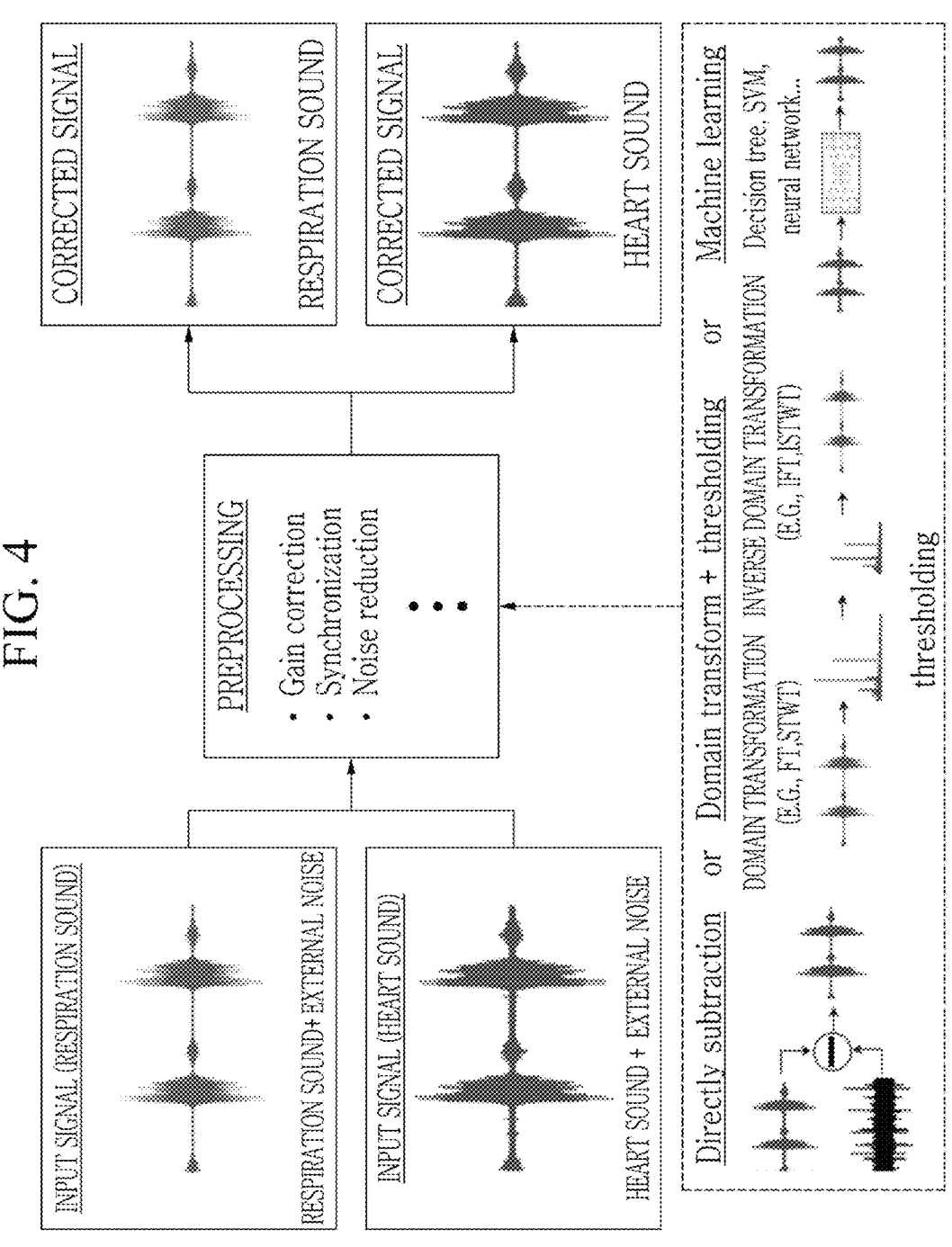
FIG. 4 is a diagram explaining a preprocessing configuration according to an embodiment.
Figure 5:
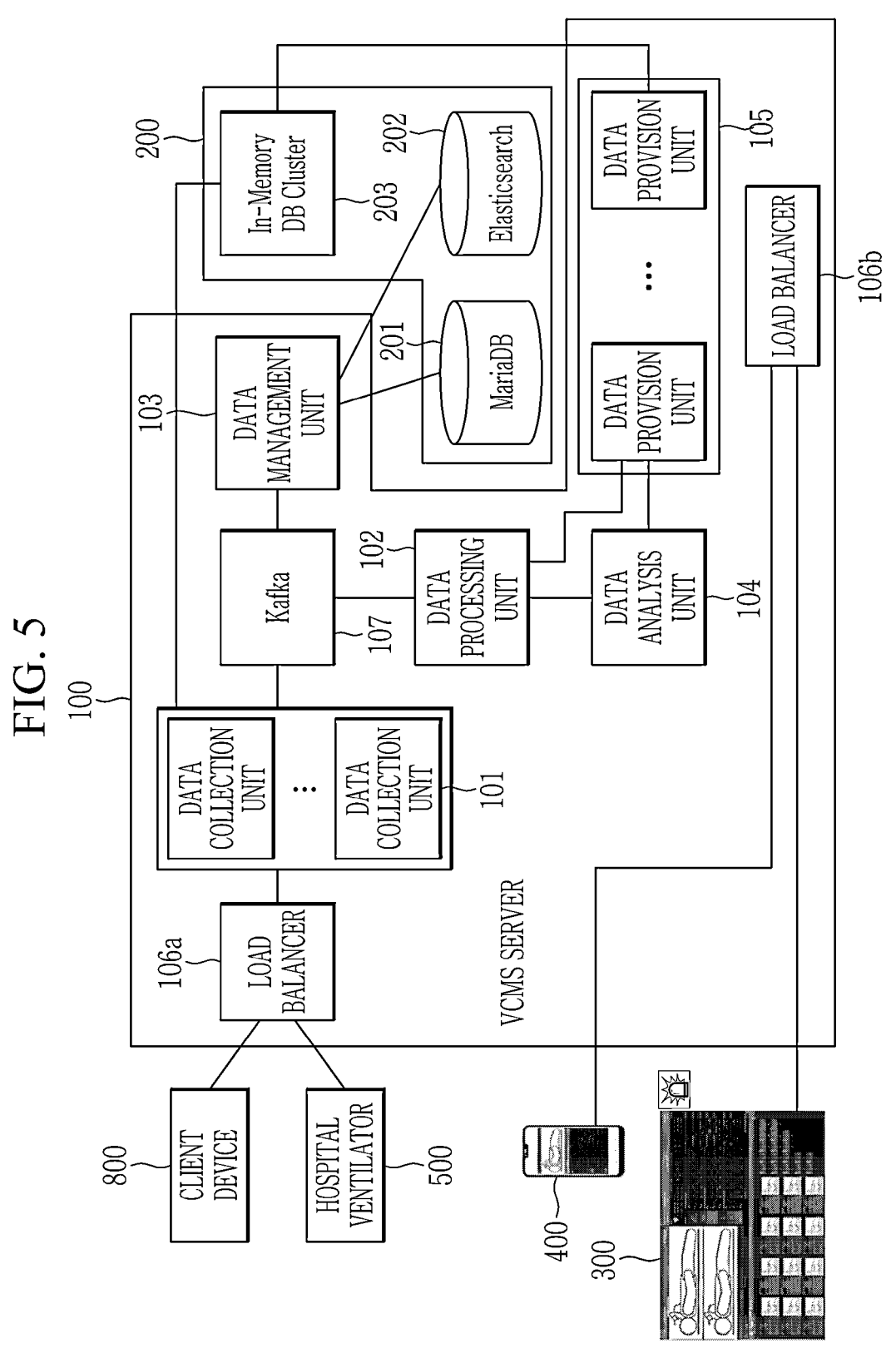
FIG. 5 is a block diagram showing a detailed configuration of an integrated monitoring server according to another embodiment.

FIG. 2 is a block diagram showing a detailed configuration of the integrated monitoring server 100 according to an embodiment; FIG. 3 is an example diagram showing a form of the collected data according to an embodiment; FIG. 4 is a diagram explaining a preprocessing configuration according to an embodiment; and FIG. 5 is a block diagram showing a detailed configuration of the integrated monitoring server 100 according to another embodiment.

Referring to FIG. 2, the integrated monitoring server 100 may include a data collection unit 101, a data processing unit 102, a data management unit 103, a data analysis unit 104, and a data provision unit 105.

The data collection unit 101 may receive the respiratory mechanics information and the biometric signal in real time from the hospital ventilator 500 and the client device 800, and output the same to the data processing unit 102.

The respiratory mechanics information may include the tidal volume (Vt), a pulse rate (PR), a respiration rate (RR), a fraction of inspired oxygen ($FiO_2$), an inspiratory flow rate (IFR), a positive end-expiratory pressure (PEEP), a peak airway pressure (PAP), saturation of percutaneous oxygen ($SpO_2$), a partial pressure of oxygen ($PaO_2$), a $SpO_2/FiO_2$ ratio (S/F ratio), a flow, or the like.

Here, the hospital ventilator 500 and the client device 800 may transmit the respiratory mechanics information and biometric signal of the patient in an encrypted form through an encryption algorithm such as a data encryption standard (DES) and an advanced encryption standard (AES), and the data collection unit 101 may decode the received respiratory mechanics information and biometric signal, and output the same to the data processing unit 102.

The data collection unit 101 may support the TCP/IP based on C#, net Framework 5.

Referring to FIG. 3, types of the signals collected by the data collection unit 101 may include a waveform of the pressure, the flow rate, or the volume, collected from the ventilator 500 or 600, and the electrocardiogram, the respiration sound, or the heart sound in a graph form and collected by the patient monitoring device 700.

The data processing unit 102 may function to correct the respiratory mechanics information and the biometric signal.

Referring to FIG. 4, the data processing unit 102 may perform a preprocessing task such as gain correction, synchronization, or noise reduction to restore and improve the input time-series respiratory mechanics information and the bio-signal information from distorted information.

In particular, a representative task for the noise reduction may be performed by directly measuring and removing external noise and signal. Here, the external noise may be measured by installing a noise measurer at each remote location and measuring the external noise in the data.

In addition, the preprocessing task for the noise reduction may be performed by transforming the time-series information to another domain (e.g., a fourier domain, or a wavelet domain), then specifying a threshold value of removing a value of a predetermined value or less, and then inversely transforming the same.

In addition, the preprocessing task for the noise reduction may be performed by at least one method of reducing a noise component by using machine learning (ML).

After this process, the data processing unit 102 may process signal data into an optimal state to finally determine a signal feature.

Here, signal data processing may involve a task of analyzing/processing the patient respiration state into a signal format in which the patient respiration state may be identified.

The signal data processing may primarily include a process of analyzing the threshold value, period, height, or the like of the signal to determine the patient respiration state.

In addition, the signal data processing may include a domain transformation process such as mel-frequency cepstrum (MFC) or wavelet transform when complex analysis is required between the patient respiration and the respiration signal.

The data processing unit 102 may output the preprocessed real-time respiratory mechanics information and biometric signals to each of the data management unit 103, the data analysis unit 104, and the data provision unit 105.

In addition, the data processing unit 102 may perform the preprocessing of converting the respiratory mechanics information into a health level 7 (HL7) protocol and make the same usable by the hospital system 300.

The HL7 protocol may be a protocol that allows electronic exchange based on a standardized communication rule to enable information exchange and compatibility of heterogeneous medical devices that are not connected to an external medical device, that is, a hospital server.

The data processing unit 102 may be equipped with a fast processing speed and a data loss prevention function, and may utilize an open source such as Kafka or Apache License 2.0.

The data management unit 103 may store, in the database server 200, the respiratory mechanics information and biometric signal, from which the noise is removed and which is processed into the optimal state, by the data processing unit 102.

The data management unit 103 may store monitoring data for each device in a database server 200 (e.g., non SQL (NoSQL)), and provide a historical data inquiry service through a web application. Here, the implementation of the web application may be separately developed as a separate module for a monitoring function. The data management unit 103 may be operated based on Java Application, and is not limited thereto.

In addition, the data management unit 103 may function to manage the identification information (or the device identifier) of each of the devices 500, 600, 700, and 800 connected to each other to collect the registration information (or the patient identifier) of the patient and the bio-signal of the patient to identify a target patient of the respiratory mechanics information and the biometric signal, and identify the device 500, 600, 700, or 800 transmitting or receiving the information. The patient identifier and device identifier of the patient may be stored in the database server 200, and the respiratory mechanics information and the biometric signals may be transmitted by being matched with the patient identifier and the device identifier.

The data analysis unit 104 may analyze the preprocessed respiratory mechanics information and biometric signal, and output abnormal symptom occurrence information to the data provision unit 105 when the abnormal symptom occurs that has a value more than the threshold value or satisfying a predetermined condition. The data provision unit 105 may then generate the visual and/or audible alarm to notify the abnormal symptom occurrence, and output the generated visual/audible alarm to the hospital system 300 and the mobile terminal 400.

The data provision unit 105 may generate the integrated monitoring screen displaying the preprocessed respiratory mechanics information and the biometric signal integrated to each other, and transmit the integrated monitoring screen to the hospital system 300 and the mobile terminal 400.

FIG. 5 shows an example of a system configuration which is the same as the configuration of FIG. 2, and considers that the servers are duplicated.

The plurality of data collection units 101 may be implemented and connected to a load balancer 106a. The load balancer 106a may distribute the respiratory mechanics information and biometric signal of the patient which are received from the hospital ventilator 500 and the client device 800 based on a specified load balancing algorithm, and transmit the same to each data collection unit 101.

The plurality of data provision units 105 may be implemented and connected to a load balancer 106b. The load balancer 106b may distribute a data provision result, that is, the integrated monitoring screen and the alarm information, received from one of the plurality of data provision units 105 based on the specified load balancing algorithm, and output the same to the hospital system 300 and the mobile terminal 400.

The load balancer 106a and the load balancer 106b may perform load balancing through HA Proxy when physical L4 (or layer 4) equipment cannot be introduced.

Kafka 107 may be located between the plurality of data collection units 101 and the data management unit 103. The Kafka 107 may be a large-capacity/high-speed message queue to collect each of the respiratory mechanics information and bio-signal information (e.g., waveform or parameter) of the patient. The Kafka 107 may simultaneously provide the same data to a plurality of service applications. Here, the service application may include the data management unit 103 and the data analysis unit 104.

The Kafka 107 may be mounted on the data processing unit 102 or installed in an independent component in front of the data processing unit 102.

The Kafka 107 may simultaneously provide the same data to the data processing unit 102 and the data management unit 103.

The Kafka 107 may support in-memory-based key & value storage and Pub/Sub messaging. Here, the key & value storage may perform a function of storing information (or key) such as the patient identifier and the bio-signal information (or value) for each patient. The Pub/sub messaging may correspond to a (publisher, pub) function of selecting and transferring data required for the data management unit 103 (or the subscriber, sub) and the data analysis unit 104.

The data provision unit 105 may be implemented as a RESTful API server to provide the ventilator monitoring data.

The data provision unit 105 may be equipped with a function for its link with the hospital system.

The data provision unit 105 may perform the inquiry and processing of data stored in Elasticsearch 202, and transmit its result to the mobile terminal 400.

The data provision unit 105 may provide creating, reading, updating, and deleting (CRUD) functions of data in Maria database (DB) 201.

The data provision unit 105 may be implemented as a web application server providing a user interface (UI) for providing the ventilator monitoring data, and operated by being changed to a C#-based local application rather than a browser when a delay occurs in the data inquiry.

When determining that the respiration is not normal, the data analysis unit 104 may perform an operation required for the remote control to restore the normal respiration.

According to an embodiment, the data analysis unit 104 may analyze the preprocessed data, and when determining that the respiration is not normal, the data analysis unit 104 may generate remote control data for restoring the normal respiration, and transmit the remote control data to the client device 800 through the data provision unit 105. For example, the remote control data may include information for controlling the ventilator 500 or 600 to regulate the oxygen supply amount and oxygen concentration of the ventilator 500 or 600.

In addition, the data analysis unit 104 may analyze the preprocessed data, and when recognizing a situation in which the remote control of the medical personnel is required, the data analysis unit 104 may transmit a remote control mode request to the mobile terminal 400 owned by the medical personnel through the data provision unit 105. The medical personnel may then directly control the hospital ventilator 500. Alternatively, the mobile terminal 400 may be connected to the home ventilator 600 through the client device 800 or may access to the client device 800 through the hospital server (not shown), and the medical personnel may remotely control the home ventilator 600 to perform an operation to maintain and restore the normal respiration.

In addition, when determining that the respiration is not normal or a connection tube of the ventilator 600 is sepa-rated, the data analysis unit 104 may transmit alarm data, such as information guiding a guardian to take an instruction such as an instruction to connect the connection tube or emergency notification, to a pre-registered guardian terminal (not shown) through the data provision unit 105.

In addition, when determining that an emergency situation occurs, the data analysis unit 104 may transmit a notification alarm to a pre-registered hotline hospital institution server or terminal (not shown) through the data provision unit 105.

The database server 200 may include the Maria DB 201, the Elasticsearch 202, and an in-memory DB cluster 203.

The Maria DB 201 may be an open source relational database management system (RDBMS), and implemented as a database for standardized data management.

The Maria DB 201 may store the real-time received respiratory mechanics information and the biometric signal by the data management unit 103.

The Maria DB 201 may store the monitoring data of the ventilator 500 or 600.

The Maria DB 201 may process the respiratory mechanics information, the biometric signal, and the ventilation monitoring data into inquiry data and store the same.

The Maria DB 201 may provide data requested for search by the Elasticsearch 202 to the data provision unit 105.

The Elasticsearch 202 may perform data search and data request to the Maria DB 201.

The Elasticsearch 202 may be the non SQL (NoSQL) for a document-based search engine in Json format, and may provide RESTful-based Query DSL in link with the data provision unit 104.

The in-memory DB cluster 203 may be a memory DB for ventilator connection management, and configured for smooth connection between the servers when the servers are duplicated. The server 200 including the in-memory DB cluster 203 may receive and store the collected data and transfer the data to the data provision unit 105.

The data collection unit 101 may collect the data and transfer the same to the Kafka 107. The Kafka 107 may transfer the instruction to the data collection unit 101.

The data transferred to the Kafka 107 may be transferred to the data processing unit 102, and the data preprocessed by the data processing unit 102 may be transferred to the data provision unit 105.

In addition, the data transferred to the Kafka 107 may be transferred to the data processing unit 102, the data preprocessed in the data processing unit 102 may be transferred to the data analysis unit 104, and a data analysis result by the data analysis unit 104 may be transferred to the data provision unit 105.

A process in which the data is transferred from the Kafka 107 to the data processing unit 102 or/and the data analysis unit 104, or a configuration in which the data is transferred from the data processing unit 102 or/and the data analysis unit 104 to the data provision unit 105 may correspond to a backend configuration.

A configuration in which the data is transferred from the data management unit 103 to the data provision unit 105, or the data is provided from the data provision unit 105 to the hospital system 300 and the mobile terminal 400 may correspond to a frontend configuration.

The backend may be implemented as an application programming interface (API) server module for its communication with the frontend, and transfer the data to the front end implemented on a web through a web socket to provide and display the data to the hospital system 300 and the mobile terminal 400.

FIG. 6 is a flowchart showing an operation of the integrated monitoring server according to an embodiment.

Referring to FIG. 6, the data collection unit 101 may collect the time-series ventilation measurement data, that is, the respiratory mechanics information, from the ventilator 500 or 600, and collect time-series sensing data of the patient, that is, the bio-signal information of the patient from the patient monitoring device 700 (S101).

The data processing unit 102 may perform the preprocessing task of removing a noise from the collected data (in S101) and processing the same into an optimal state (S102).

The data management unit 103 may store the preprocessed wave or numeric type respiratory mechanics information and bio-signal information in the database server 200 (S103).

The data provision unit 105 may generate the real-time monitoring screen displaying the preprocessed respiratory mechanics information and bio-signal information (in S103), and transmit the generated real-time monitoring screen to the user mobile terminal 400 and the hospital system 300 (S104).

In addition, in parallel with S104, the data analysis unit 106 may perform the data analysis to determine whether the preprocessed respiratory mechanics information and bio-signal information (in S103) satisfy the specified threshold value or abnormality condition (S105), and may instruct the data provision unit 105 to output the visual/audible alarm expressing the data analysis result (S106).

In addition, in parallel with S104 and S105/S106, the data provision unit 105 may provide the inquiry service of the stored data of the patient through a web UI or a mobile UI (S107).

Here, FIGS. 7 to 16 show another embodiment of the data analysis unit 104, which may be added to the embodiment of FIGS. 1 to 6.

Figure 7:
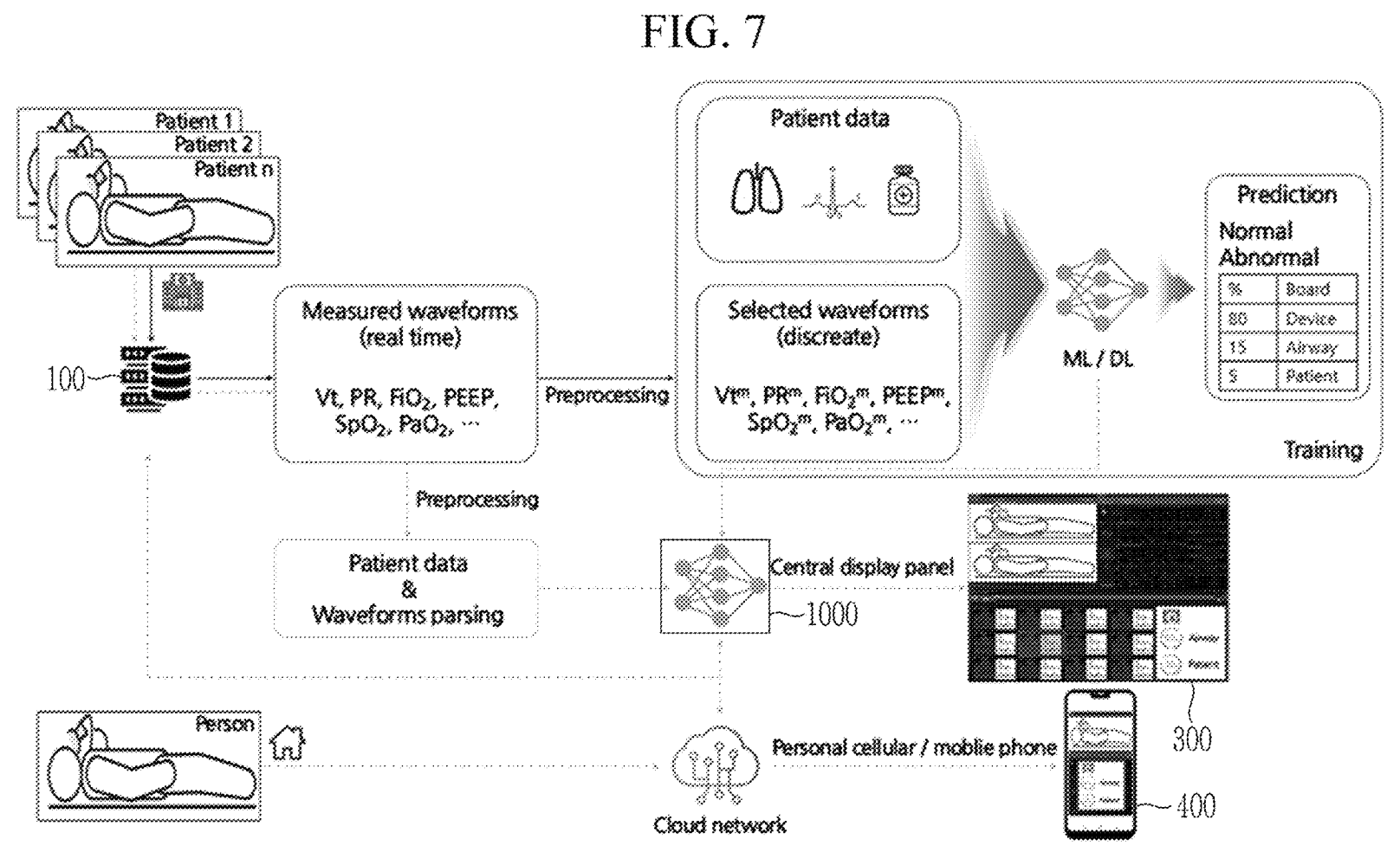

FIG. 7 is a conceptual diagram showing ventilator data analysis using artificial intelligence technology according to an embodiment.

Referring to FIG. 7, the integrated monitoring server 100 may collect patient information including the respiratory mechanics information and biometric signals of the plurality of patients with the waveforms, patient state information, medical personnel opinions about the patient, or the like, preprocess the collected data, and use the preprocessed data as the learning data to train an artificial intelligence model 1000.

The artificial intelligence model may be a machine learning model and/or a deep learning model, and is not limited to these model types.

According to an embodiment, the trained artificial intelligence model 1000 may perform at least one of normal signal/abnormal signal determination, abnormal signal occurrence cause type classification, and specific disease prediction from the input data. This artificial intelligence model 1000 may be referred to as an abnormal signal detection model 1001. A data analysis configuration using the abnormal signal detection model 1001 is described below with reference to FIGS. 8 to 11.

According to another embodiment, the artificial intelligence model 1000 may be classified into a model performing the normal signal/abnormal signal determination and the abnormal signal occurrence cause type classification from the input data, and a model performing the specific disease prediction. This artificial intelligence model 1000 may be referred to as a disease prediction model 1002. A data analysis configuration using the disease prediction model 1002 is described below with reference to FIGS. 12 to 16.

The integrated monitoring server 100 may transmit output of the artificial intelligence model 1000, that is, at least one of the normal signal/abnormal signal determination, the abnormal signal occurrence cause type classification (i.e., device, airway, patient, or %), and the specific disease prediction, to the hospital system 300 and/or the mobile terminal 400.

In addition, when determining that a corresponding signal is an abnormal signal or classifying that a corresponding cause is an abnormal signal occurrence cause type that requires an emergency alarm, the integrated monitoring server 100 may generate the visual/audible alarm notifying an emergency situation or requiring an emergency action and transmit the same to the hospital system 300 or/and the mobile terminal 400.

The visual alarm may be output in a form of a warning screen through a predetermined thumbnail or a pop-up window.

Here, the learning and classification/prediction of the artificial intelligence model 1000 may be implemented by the data analysis unit 104.

Figure 8:
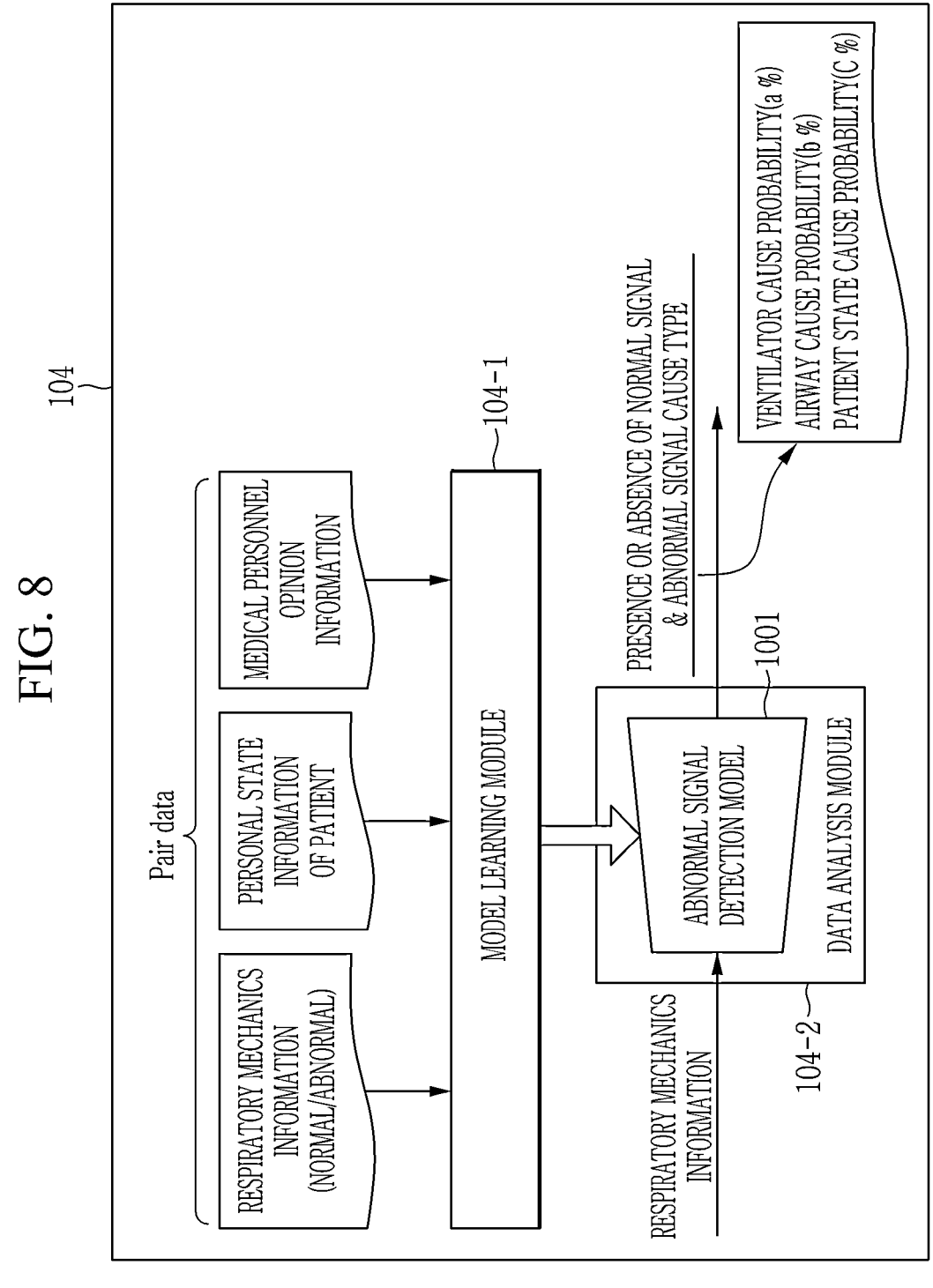
FIG. 8 is a block diagram of a data analysis unit performing data analysis by using an abnormal signal detection model according to an embodiment.
Figure 9:
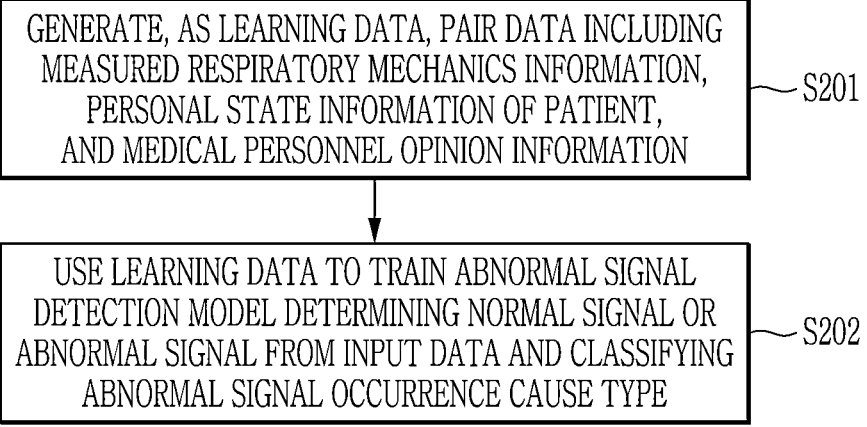
FIG. 9 is a flowchart showing a learning procedure of the abnormal signal detection model according to an embodiment.
Figure 10:
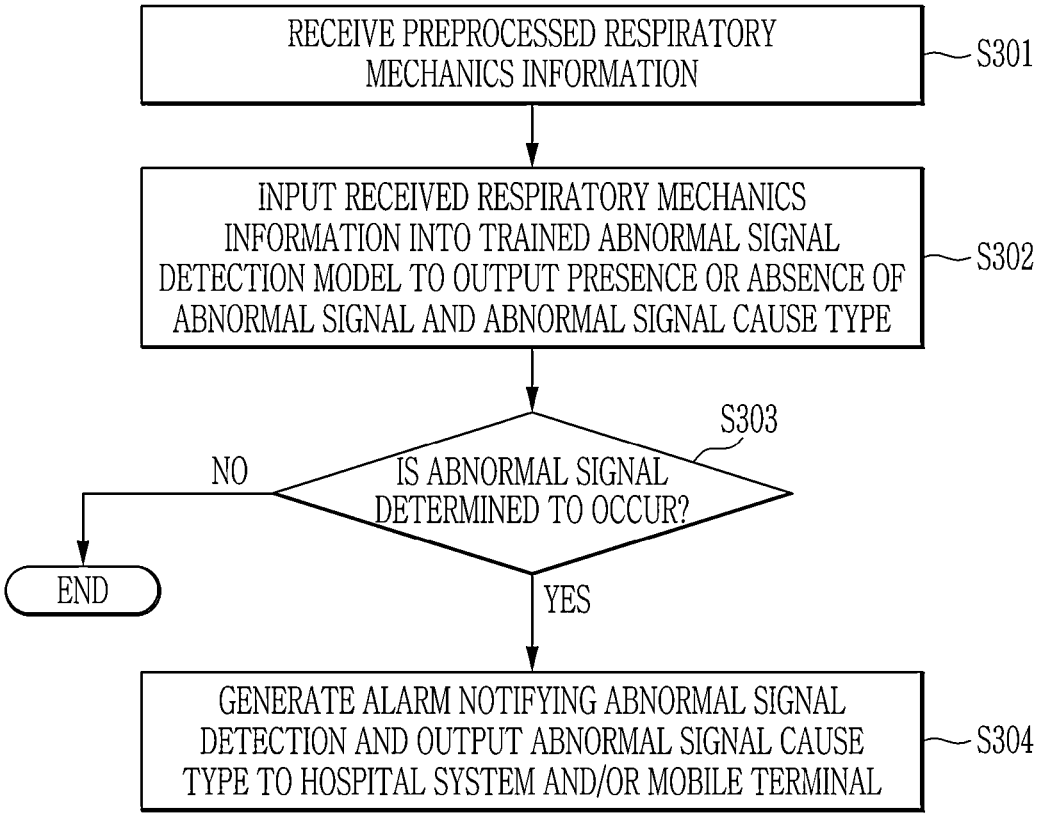
FIG. 10 is a flowchart showing an abnormal signal analysis procedure using the abnormal signal detection model according to an embodiment.

FIG. 8 is a block diagram of the data analysis unit performing the data analysis by using the abnormal signal detection model according to an embodiment; FIG. 9 is a flowchart showing a learning procedure of the abnormal signal detection model according to an embodiment; and FIG. 10 is a flowchart showing an abnormal signal analysis procedure using the abnormal signal detection model according to an embodiment.

Referring to FIG. 8, the data analysis unit 104 may include a model learning module 104-1 and a data analysis module 104-2.

The model learning module 104-1 may have respiratory mechanics information of a normal person, the respiratory mechanics information of the patient, personal state information of the patient, and medical personnel opinion information on the patient as pair data, use the pair data as the learning data to perform the learning in a deep learning or machine learning (ML) manner, thus generating the abnormal signal detection model 1001.

The respiratory mechanics information of the patient may be used when the model learning module 104-1 learns the respiratory mechanics information measured in real time through the hospital ventilator 500 or the home ventilator 600.

The abnormal signal detection model 1001 may be an artificial intelligence model trained to classify the presence or absence of the abnormal signal and an abnormal signal occurrence cause type from the input data.

The abnormal signal detection model 1001 may receive the respiratory mechanics information and output the presence or absence of the abnormal signal or the abnormal signal occurrence cause type based on the input data.

The abnormal signal occurrence cause type may include a ventilator cause (or a ventilator device), an airway cause, and an abnormal patient respiration state cause type. The abnormal signal occurrence cause may be a problem with the ventilator device itself, such as a problem with inflow oxygen due to a problem with an air compressor of the ventilator or a respiration synchronization problem of the patient who has difficulty in spontaneous respiration.

The abnormal signal occurrence cause may be a problem with the airway that moves oxygen and carbon dioxide, such as separation or bending of an airway tube.

The abnormal signal occurrence cause may be the patient state, for example, an abnormal respiration sound such as bronchial respiration, coarse crackle, fine crackle, wheeze, stridor, or rhonchus.

The abnormal signal detection model 1001 may output the abnormal signal occurrence cause type in a form of probability information for each type, such as the ventilator cause (a %), the airway cause (b %), and the abnormal patient respiration state cause type (c %).

The abnormal signal detection model 1001 may learn a relationship between feature information of the respiratory mechanics information and the abnormal signal occurrence cause, the respiratory mechanics information including the tidal volume (Vt), the pulse rate (PR), the respiration rate (RR), the fraction of inspired oxygen (FiO$_2$), the inspiratory flow rate (IFR), the positive end-expiratory pressure (PEEP), the peak airway pressure (PAP), the saturation of percutaneous oxygen (SpO$_2$), the partial pressure of oxygen (PaO$_2$), the SpO$_2$/FiO$_2$ ratio (S/F ratio), the flow, or the like. The abnormal signal detection model 1001 may use, as additional learning data, the personal state information of the patient such as the age, medical history, or the like of the patient and the medical personnel opinion information after examining the patient together with the respiratory mechanics information to extract the feature information through the respiratory mechanics information, the personal state of the patient, and the medical personnel opinion information, and learn the relationship between the extracted feature information and the abnormal signal occurrence cause.

The feature information may include a signal waveform type of the respiratory mechanics information, the threshold value (e.g., maximum or minimum value) of the respiratory mechanics information, a cycle tendency of the respiratory mechanics information, and a statistical feature of the respiratory mechanics information/personal state of the patient/medical personnel opinion information, entropy of the respiratory mechanics information/personal state of the patient/medical personnel opinion information, or the like.

The model learning module 104-1 may use the learning data with the personal state of the patient and the medical personnel opinion information in a vector form. For example, when the patient is 25 years old, [zero to 10 years old, 11 years old to 20 years old, 21 years old to 30 years old, . . . , and 91 years to 100 years] may be expressed in a form of [0 0 1 0 0 0 0 0 0 0].

In order to extract a meaningful feature, the model learning module 104-1 may use an algorithm such as F-Test, analysis of Variance (ANOVA), least absolute shrinkage and selection operator (LASSO), cross-validation, first order and second order-based probabilistic feature extraction, transform-based feature extraction.

In order to lower a dimension of the feature, the model learn module 104-1 may use a passive reduction method, principal component analysis (PCA), independent component analysis (ICA), neighborhood component analysis (NCA), and an algorithm such as clustering, least absolute shrinkage and selection operator (LASSO), ridge, elastic net, or the machine learning.

The model learning module 104-1 may train the abnormal signal detection model 1001 through decision tree learning, artificial neural network, genetic algorithms, support vector machine, clustering, bayesian network, reinforcement learning, regression analysis, or the like.

The model learning module 104-1 may use the respiratory mechanics information, the personal state of the patient, and the medical personnel opinion information as the learning data to thus train a regression model or a classification model to determine the presence or absence of the abnormal signal and classify the abnormal signal occurrence cause type. Here, the trained regression model or classification model may comprehensively learn the waveform type, the threshold value, and the cycle tendency.

The model learning module 104-1 may use the respiratory mechanics information, the personal state of the patient, and the medical personnel opinion information as the learning data to thus train the deep learning model to determine the presence or absence of the abnormal signal and classify the abnormal signal occurrence cause type. Here, the deep learning model may learn a relationship between the input data (or the respiratory mechanics information) and output data (or presence or absence of the abnormal signal/abnormal signal occurrence cause type) through network training.

These regression model, classification model, and deep learning model may be output as the abnormal signal detection model 1001.

Referring to FIG. 9, the model learning module 104-1 may generate, as the learning data, the pair data including the respiratory mechanics information measured by the ventilator 500 or 600, the personal state information of the patient, and medical personnel opinion information, input from the outside (S201). Here, the respiratory mechanics information may be used as the learning data after the preprocessing process is performed by the data processing unit 102 described above.

The model learning module 104-1 may use the learning data to generate the abnormal signal detection model determining the normal signal or the abnormal signal from the input data and classifying the abnormal signal occurrence cause type (S202).

The data analysis module 104-2 may include the trained abnormal signal detection model 1001 provided by the model learning module 104-1.

Referring to FIG. 10, the data analysis module 104-2 may receive the preprocessed respiratory mechanics information from the data processing unit 102 (in FIGS. 1 to 6) (S301).

The data analysis module 104-2 may input the received respiratory mechanics information into the trained abnormal signal detection model 1001 to output the presence or absence of the abnormal signal and the abnormal signal occurrence cause type (S302).

According to an embodiment, the abnormal signal occurrence cause type may be output in a form shown in Table 1 below.

TABLE 1

| Cause type | Value (%) |
|---|---|
| Ventilator | a |
| Airway | b |
| Patient state (Abnormal respiration sound) | c |

According to another embodiment, an abnormal signal occurrence cause type with the highest probability or one abnormal signal occurrence cause type having a value more than the threshold value and having the highest value may be output as the abnormal signal occurrence cause type.

When determining that the corresponding signal (in S302) is the abnormal signal (S303), the data analysis module 104-2 may generate the alarm notifying the abnormal signal detection and output the abnormal signal occurrence cause type to the hospital system 300 and/or the mobile terminal 400 (S304).

Figure 11:
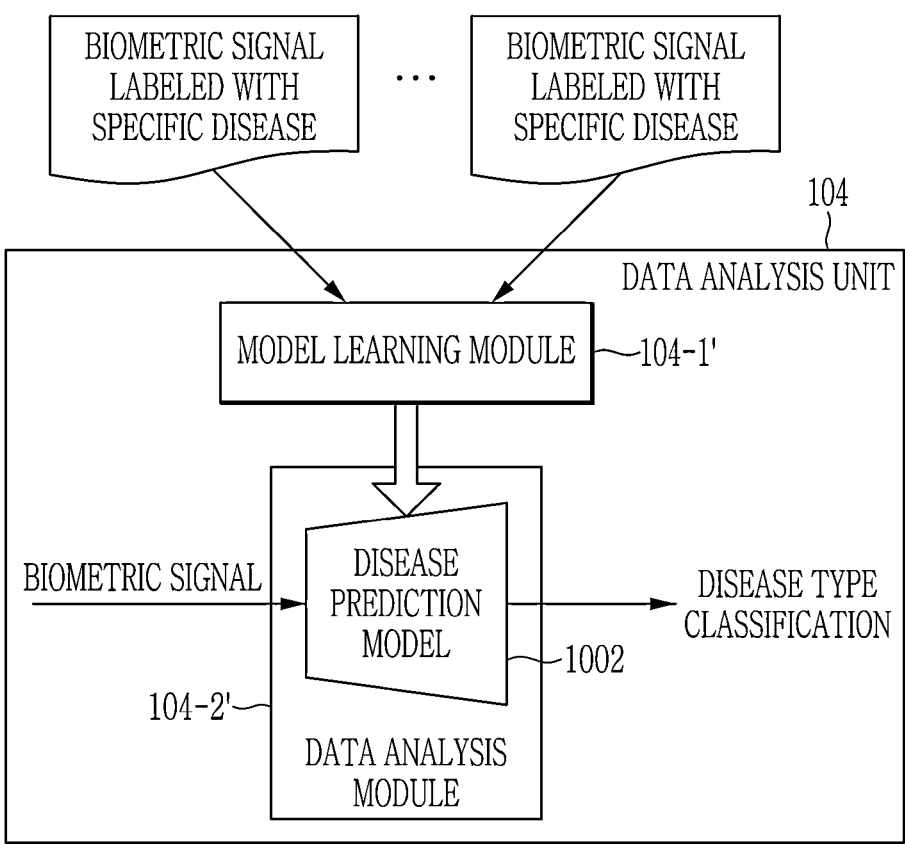
FIG. 11 is a block diagram of a data analysis unit performing data analysis using a disease prediction model according to an embodiment.
Figure 12:
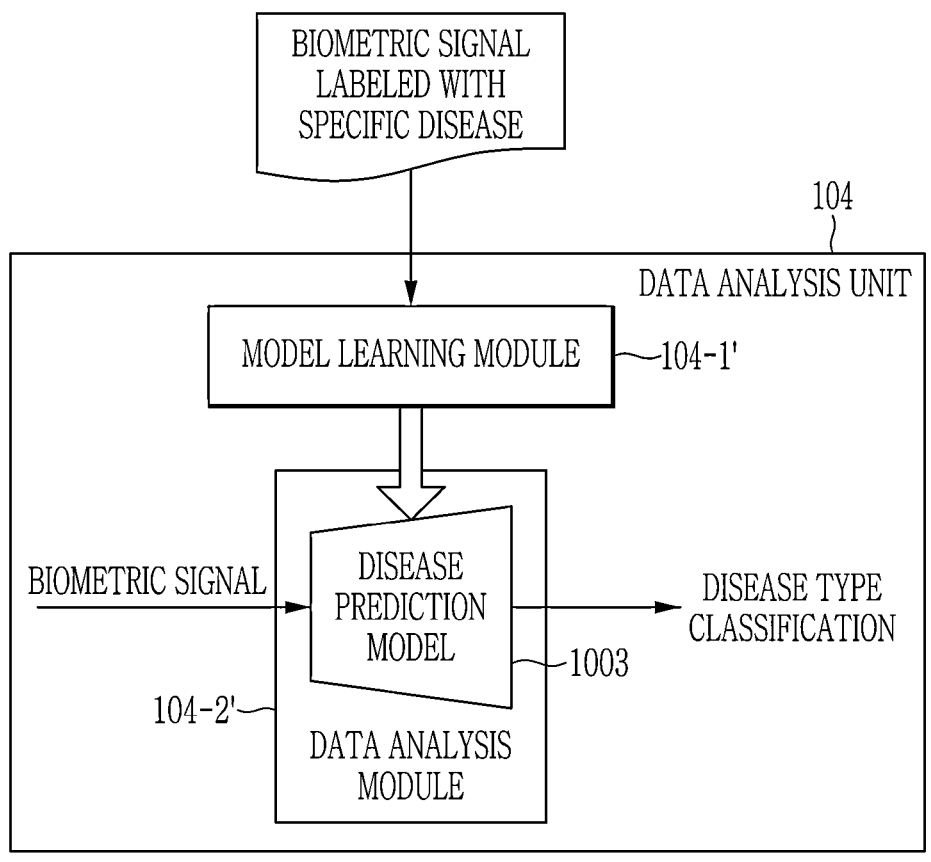
FIG. 12 is a block diagram of a data analysis unit performing data analysis using a disease prediction model according to another embodiment.

FIG. 11 is a block diagram of the data analysis unit performing the data analysis using the disease prediction model according to an embodiment; FIG. 12 is a block diagram of the data analysis unit performing the data analysis using the disease prediction model according to another embodiment; and FIG. 13 is a flowchart explaining the data analysis procedure using the disease prediction model according to an embodiment.

Referring to FIG. 11, the data analysis unit 104 may include a model learning module 104-1' and a data analysis module 104-2'.

The model learning module 104-1' may train the disease prediction model 1002 to classify a disease type from the input data by using the various biometric signals labeled with various specific diseases and the biometric signal of a normal person as the learning data.

The disease prediction model 1002 may be an artificial intelligence model trained to classify heart disease (e.g., arrhythmia disease, heart failure, heart valve disease, myocardial disease, pericardial disease, or congenital heart defect) and respiratory disease, that is, wheezing, crackle/rale, rhonchi, stridor, or the like by using the respiration sound and a respiration sound auscultation signal (e.g., normal, bronchial breath, coarse/fine crackle, wheeze, stridor, and rhonchus), or the heart sound (e.g., normal, systolic murmur, diastolic murmur, or murmur), and the electrocardiogram (e.g., sinus rhythm, atrial fibrillation, or bundle branch block) as the learning data.

The disease prediction model 1002 may be trained through analysis of a correlation between a feature extracted from the learning data and the specific disease type.

The data analysis module 104-2' may include the disease prediction model 1002.

The disease prediction model 1002 may be an artificial intelligence model trained to classify the disease type from the input data. The disease prediction model 1002 may receive the respiration sound, the heart sound, the electrocardiogram, or the like, and output the specific disease type classified based on the input data.

Referring to FIG. 12, unlike FIG. 11, an individual disease prediction model 1003 may be trained for each specific disease type. Here, the learning and analysis methods of the disease prediction model 1003 may be the same as those of FIG. 11. However, the learning data and analysis used herein are limited to the specific disease. That is, the disease prediction model 1003 may be a model predicting the respiratory disease or a model predicting the heart disease. The learning data used herein may be either the respiration sound or the heart sound/electrocardiogram.

The learning and analysis procedures common to the embodiments of FIGS. 11 and 12 are the same as those of FIG. 13. Referring to FIG. 13, the model learning module 104-1' may generate the disease prediction model 1002 or 1003 performing the disease prediction including the presence or absence of the specific disease or classification of the specific disease type from the input data by using the biometric signal of the normal person, the biometric signal labeled with the specific disease, that is, the respiration sound, and/or the heart sound/electrocardiogram as the learning data (S401).

In S401, the model learning module 104-1' may generate the disease prediction models 1002 and 1003 classifying the presence or absence of the heart disease and/or a heart disease type such as the arrhythmia disease, the heart failure, the heart valve disease, the myocardial disease, the pericardial disease, or the congenital heart defect by using an electrocardiogram signal, and the presence or absence of the respiration disease and/or a respiratory disease type such as the wheezing, the crackle/rale, the rhonchi, or the stridor by using the respiration sound auscultation signal.

In S401, the model learning module 104-1' may analyze the correlation between the disease and various features of the measured signal such as its waveform type, threshold value, cycle tendency, and transform a domain like a mel-frequency cepstrum coefficient (MFCC) to thus derive a new feature of an input signal, thus performing a process of finding its correlation with the disease.

The data analysis module 104-2' including the disease prediction model 1002 or 1003 generated in S401 may receive the preprocessed biometric signal from the data processing unit 102 (in FIGS. 1 to 6) (S402).

The data analysis module 104-2' may input the biometric signal received in S402 into the trained disease prediction model 1002 or 1003 to perform the disease prediction including the presence or absence of the specific disease or the classification of the specific disease type (S403).

The data analysis module 104-2' may output disease prediction information acquired in S403 to the hospital system 300 and/or the mobile terminal 400 (S404).

Figure 14:
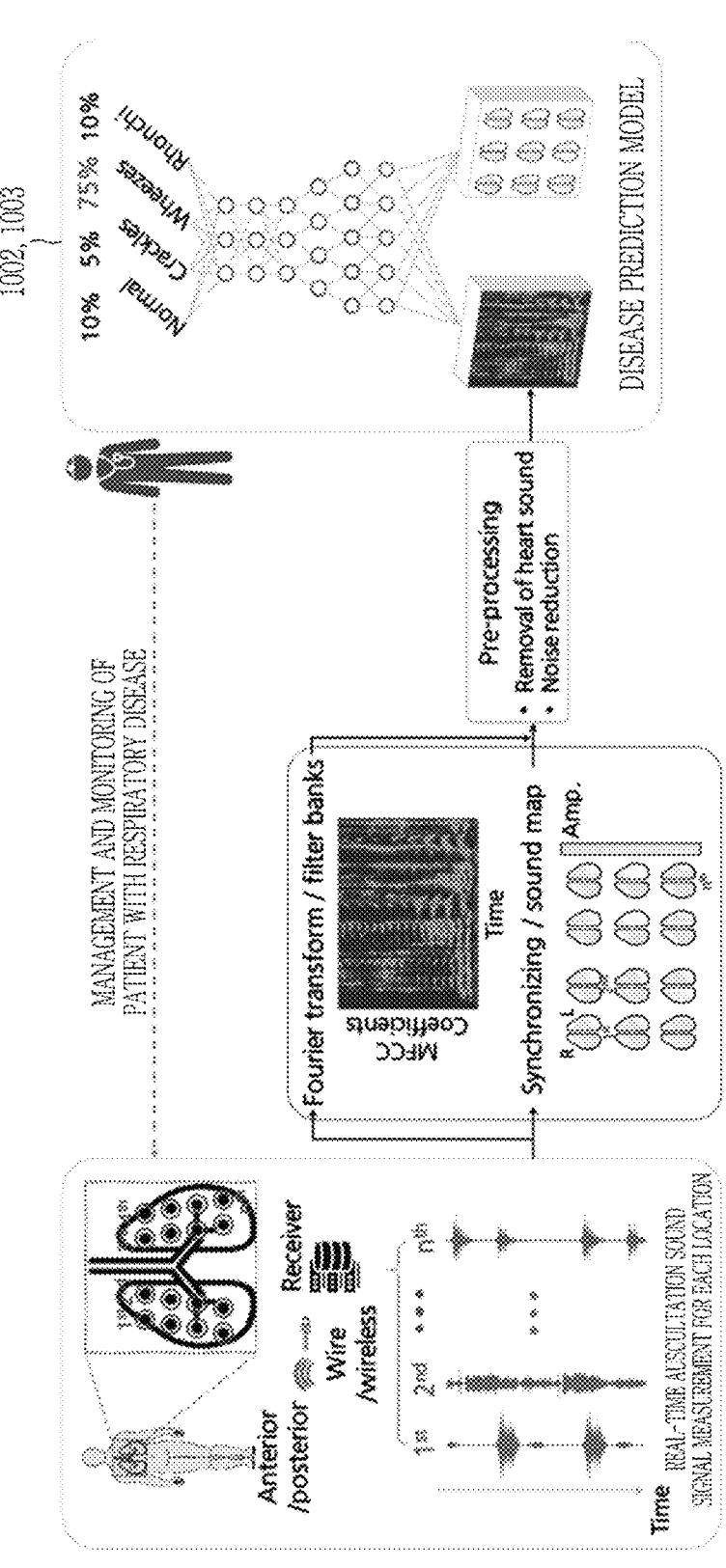
FIG. 14 is a conceptual diagram explaining a respiratory disease prediction according to an embodiment.
Figure 15:
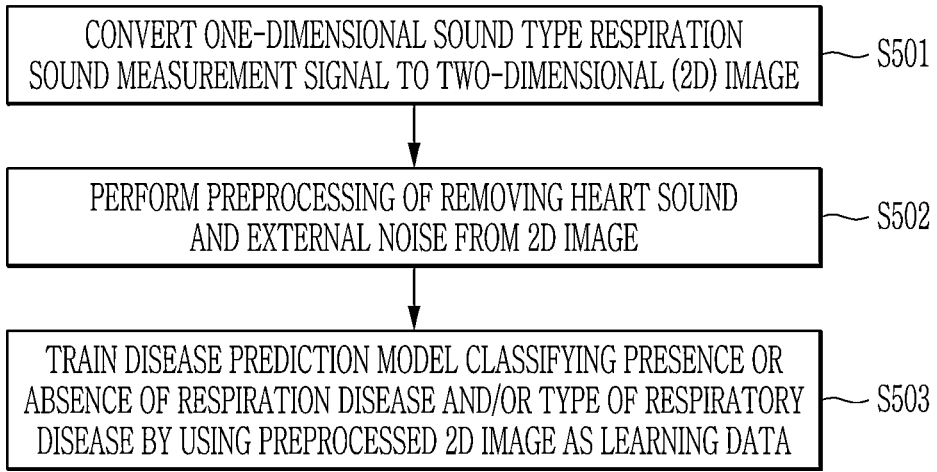
FIG. 15 is a flowchart explaining the learning procedure of a respiratory disease prediction model according to an embodiment.
Figure 16:
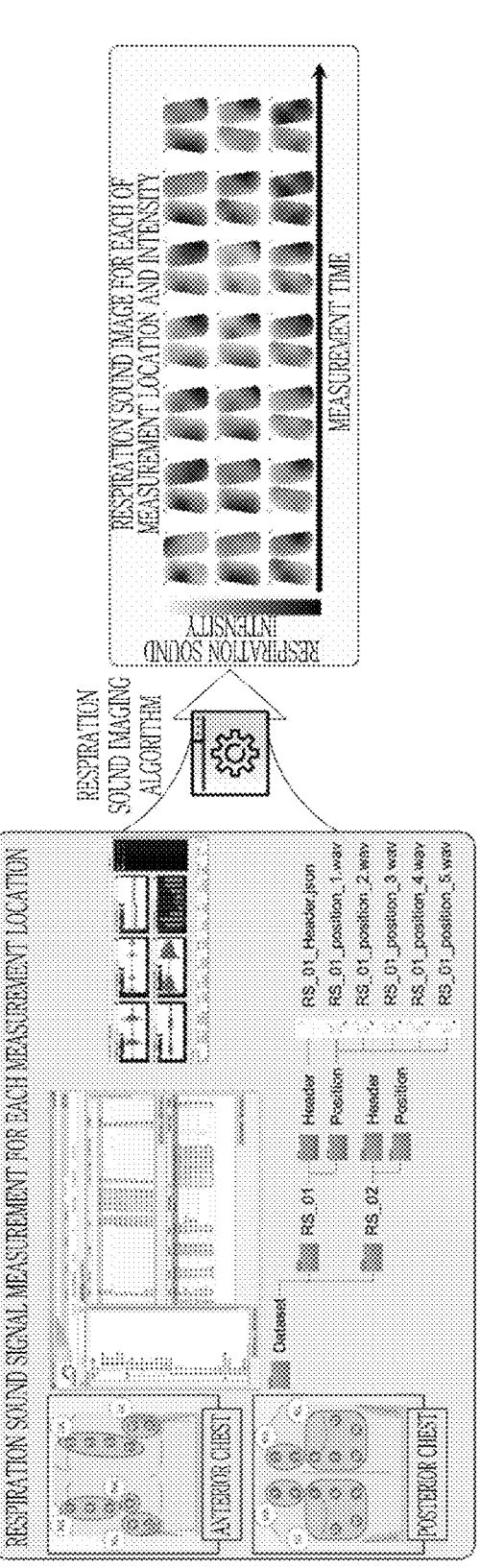
FIG. 16 is a conceptual diagram explaining a respiration sound imaging algorithm according to an embodiment.

FIG. 14 is a conceptual diagram explaining a respiratory disease prediction according to an embodiment; FIG. 15 is a flowchart explaining the learning procedure of a respiratory disease prediction model according to an embodiment; and FIG. 16 is a conceptual diagram explaining a respiration sound imaging algorithm according to an embodiment.

Here, a procedure of FIG. 15 may be another embodiment included in the disease prediction model 1002 or 1003 of FIGS. 11 to 13.

Referring to FIG. 14, when predicting the respiratory disease, the disease prediction model 1002 or 1003 may be trained to determine/classify normal respiration, the wheezing, the crackle/rale, the rhonchi, or the stridor after measuring the real-time auscultation sound signal for each location from anterior and posterior chest images (x-ray), and preprocessing the measured auscultation sound signal.

The model learning module 104-1' may convert one-dimensional sound measurement data to a two-dimensional (2D) image and use the same as the learning data to extract a number of features that show a significant correlation between the measured multi-channel respiration sound signal and the respiration disease, which is described below with reference to FIG. 15.

Referring to FIG. 15, the model learning module 104-1' may convert a one-dimensional sound type respiration sound measurement signal to the 2D image (S501).

Methods for converting the respiration sound measurement signal to the 2D image may be broadly classified into two types. The model learning module 104-1' may convert the respiration sound measurement signal to the 2D image by using the multi-channel respiration sound signal as the mel-frequency cepstrum through fourier transform and a mel filter bank. In addition, the model learning module 104-1' may convert the respiration sound measurement signal to the 2D image by using a sound map that reflects a respiration sound measurement location and signal magnitude information.

The model learning module 104-1' may perform preprocessing of removing the heart sound and the external noise from the 2D image (S502).

In S502, the preprocessing may be performed using a band-stop filter, a non-linear filter, data-driven approach, or the like.

Referring to FIG. 16, the model learning module 104-1' may image the multi-channel respiration sound measurement signal for the measurement position in the anterior and posterior chest images through S501 and S502, and generate a respiration sound image for the measurement location and respiration sound intensity based on a measurement time.

The model learning module 104-1' may measure the multi-channel respiration sound signal for each time, as shown in FIG. 16, by reflecting the location and magnitude of the measurement signal. The number of the measurement locations may be changed based on a situation.

Referring back to FIG. 15, the model learning module 104-1' may train the disease prediction model 1002 or 1003 classifying the presence or absence of the respiration disease and/or the respiratory disease type by using the preprocessed 2D image as the learning data (S503).

In S503, the model learning module 104-1' may extract the feature through a convolution neural network (CNN) and classify the disease through a fully connected layer (FC) for the improved automatic labeling and disease prediction for the respiration sound, implement a deep learning algorithm for the prediction, regulate the parameter, and perform network comparison.

In addition, the model learning module 104-1' may accurately predict the respiratory disease of the patient in real time by utilizing a high-performance algorithm, and select a stable network through k-fold cross validation.

Hereinabove, the respiration sound is described with reference to FIG. 15, and the same method may be applied to the heart sound.

Figure 17:
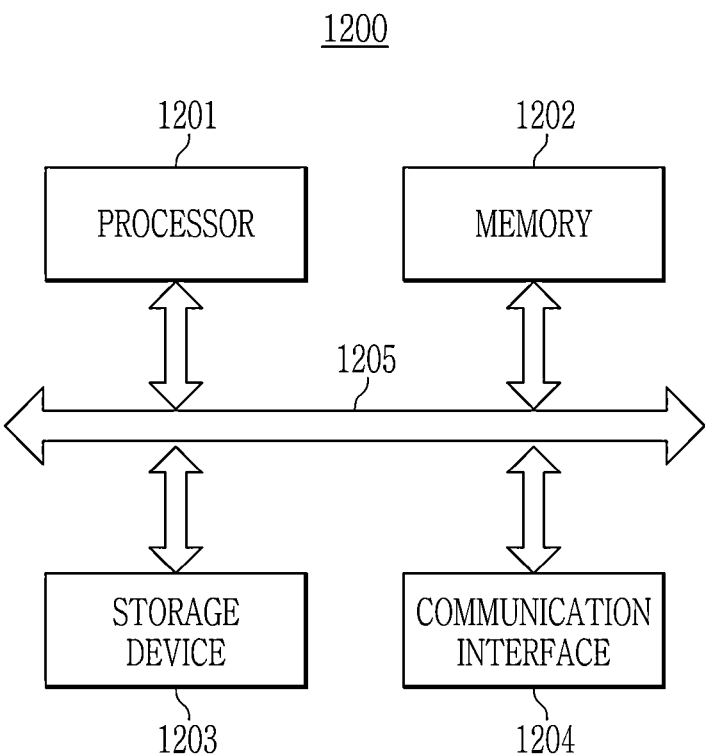
FIG. 17 is a block diagram showing a hardware configuration of a computing device according to another embodiment.

Meanwhile, FIG. 17 is a block diagram showing a hardware configuration of a computing device according to another embodiment.

Referring to FIG. 17, the integrated monitoring server 100 described with reference to FIGS. 1 to 16 may be implemented in a computing device 1200. The computing device 1200 may include at least one processor 1201, a memory 1202 for loading a computer program executed by the processor 1201, a storage device 1203 for storing the computer program and various data, a communication interface 1204, and a bus 1205 connecting these components to each other. In addition, the computing device 1200 may further include various components.

When loaded into the memory 1202, the computer program may include instructions for causing the processor 1201 to perform the methods/operations according to the various embodiments of the present disclosure. That is, the processor 1201 may execute the instructions to thus perform the methods/operations according to the various embodiments of the present disclosure. The computer program may include a series of computer-readable instructions grouped for each function and be executed by the processor.

The computer program may include the instructions for receiving the waveform-type respiratory mechanics information from the ventilator of the patient that is installed at the remote location, receiving the various biometric signals measured in real time from the patient monitoring device installed at the remote location, performing the preprocessing of removing the noise from the received respiratory mechanics information and biometric signal, and processing the same into the specified format, and transmitting the integrated monitoring screen displaying the preprocessed respiratory mechanics information and biometric signal to the hospital system or the mobile terminals of the medical personnel.

Here, the computer program may include the instructions for further performing the preprocess to convert the respiratory mechanics information to a health level 7 (HL7) protocol which is a form usable by the hospital system, and outputting the respiratory mechanics information converted to the H7 protocol in real time to the hospital system or the mobile terminal.

The computer program may include the instructions for performing the data analysis to determine whether the preprocessed respiratory mechanics information and/or biometric signals satisfy the specified threshold value or abnormal symptom condition, and transmitting the visual alarm or the audible alarm expressing the data analysis result to the mobile terminals of the medical personnel or the hospital system.

The computer program may include the instructions for performing the data analysis to classify the abnormal signal occurrence cause type from the respiratory mechanics information and/or classify the specific disease type from the biometric signal by using the artificial intelligence model trained to classify the abnormal signal occurrence cause type or the specific disease type from the input data, and transmitting the data analysis information to the hospital system or the mobile terminals of the medical personnel.

The computer program may include the instructions for converting the respiration sound measurement signal of a one-dimensional sound type to the 2D image, performing the preprocess of removing the noise from the converted 2D image, and using the preprocessed 2D image as the learning data to train the disease prediction model classifying the presence or absence of the respiration disease and/or the respiratory disease type from the input data.

The computer program may include the instructions for classifying the presence or absence of the specific disease or the disease type of the patient by inputting the biometric signal including at least one of the respiration sound, heart sound, and electrocardiogram of the patient into the disease prediction model.

The computer program may include the instructions for generating the abnormal signal detection model trained to classify the presence of the abnormal signal or the abnormal signal occurrence cause type from the input data, and classifying the presence or absence of the abnormal signal or the abnormal signal occurrence cause type by inputting the received respiratory mechanics information into the abnormal signal detection model.

The computer program may include the instructions for generating the pair data including the measured respiratory mechanics information, the personal state information of the patient, and the medical personnel opinion information as the learning data, and generating the abnormal signal detection model by using the generated learning data.

The processor 1201 may control an overall operation of each component of the computing device 1200. The processor 1201 may include at least one of a central processing unit (CPU), a micro processor unit (MPU), a micro controller unit (MCU), a graphic processing unit (GPU), or any type of processor well known in the art to which the present disclosure pertains. In addition, the processor 1201 may perform calculations on at least one application or computer program to execute the methods/operations according to the various embodiments of the present disclosure.

The memory 1202 may store various data, instructions and/or information. The memory 1202 may load one or more computer programs from the storage device 1203 to perform the methods/operations according to the various embodiments of the present disclosure.

The memory 1202 may be implemented as a volatile memory such as a random access memory (RAM), and the scope of the present disclosure is not limited thereto.

The storage device 1203 may non-temporarily store the computer program.

The storage device 1203 may include a non-volatile memory such as a read only memory (ROM), an erasable programmable ROM (EPROM), an electrically erasable programmable ROM (EEPROM), or a flash memory, a hard disk, a removable disk, or any form of computer-readable recording medium well known in the art to which the present disclosure pertains.

The communication interface 1204 may support internet communication of the computing device 1200 in the wired or wireless manner. In addition, the communication interface 1204 may support various communication methods other than the internet communication. To this end, the communication interface 1204 may include a communication module well known in the art to which the present disclosure pertains.

The bus 1205 may provide a communication function between the components of the computing device 1200.

The embodiments of the present disclosure described above are not only implemented through the devices and the methods, and may also be implemented through a program that implements the function corresponding to the configuration of the embodiment of the present disclosure or a recording medium on which the program is recorded.

Although the embodiments of the present disclosure have been described in detail hereinabove, the scope of the present disclosure is not limited thereto. That is, various modifications and alterations made by those skilled in the art that use a basic concept of the present disclosure as defined in the following claims also fall within the scope of the present disclosure.

What is claimed is:

1. A method of operating an integrated monitoring server operated by at least one processor, the method comprising:
   receiving waveform-type respiratory mechanics information in real time from a ventilator of a patient that is installed at a remote location;
   receiving a biometric signal including at least one of a respiration sound, heart sound, or electrocardiogram of the patient from a patient monitoring device installed at the remote location;
   classifying presence or absence of a specific disease or a disease type of the patient from the biometric signal by using an artificial intelligence model including a disease prediction model trained to classify the presence or absence of the specific disease or the disease type from input data;
   transmitting the real-time received waveform-type respiratory mechanics information and analysis information including the presence or absence of the specific disease or the disease type of the patient to a hospital system connected to the server through a dedicated line or a mobile terminal of medical personnel connected to the server through an internet,
   wherein the disease prediction model is configured to be trained by:
   converting a one-dimensional sound type respiration sound measurement signal to a two-dimensional (2D) image;
   performing preprocessing of removing a first noise from the converted 2D image; and
   training the disease prediction model using the preprocessed 2D image as first learning data.

2. The method of claim 1, between the receiving and the transmitting, further comprising performing preprocessing of removing a second noise from the real-time received respiratory mechanics information and processing the information into a specified format,
   wherein in the transmitting,
   the preprocessed real-time received respiratory mechanics information is transmitted.

3. The method of claim 2, wherein
   in the receiving,
   various biometric signals of the patient are further received from a patient monitoring device installed at the remote location and preprocessed, and
   in the transmitting,
   an integrated monitoring screen displaying the preprocessed respiratory mechanics information and biometric signal are generated, and the integrated monitoring screen is transmitted.

4. The method of claim 2, wherein
   in the preprocessing,
   an external noise is measured, and the second noise is removed from the real-time received respiratory mechanics information by using the measured external noise.

5. The method of claim 2, wherein
   the preprocessing comprises:
   transforming time-series information to another domain;
   specifying a threshold value; and
   removing a signal of the threshold value or less from the time-series information.

6. The method of claim 2, wherein
   in the preprocessing,
   a noise component is removed using machine learning.

7. The method of claim 2, wherein
   in the preprocessing,
   the respiratory mechanics information is converted to a health level 7 (HL7) protocol which is a form usable by the hospital system.

8. The method of claim 2, after the preprocessing, further comprising:
   performing data analysis to determine whether the preprocessed data satisfies a threshold value or abnormal symptom condition; and transmitting a visual or audible alarm expressing a data analysis result to the mobile terminal of the medical personnel or the hospital system.

9. The method of claim 2, after the transmitting,
   further comprising providing an inquiry service for stored data of the patient through a web user interface or a mobile user interface.

10. The method of claim 1, after the real-time receiving, further comprising:
   determining whether an abnormal signal occurs in the received respiratory mechanics information and classifying an abnormal signal occurrence cause type by using an abnormal signal detection model trained to classify the presence or absence of the abnormal signal or the abnormal signal occurrence cause type from input data; and
   transmitting analysis information including the presence or absence of the abnormal signal or the abnormal signal occurrence cause type to the hospital system or the mobile terminal.

11. The method of claim 10, before the classifying, further comprising:

generating, as second learning data, pair data including measured respiratory mechanics information, personal state information of the patient, and medical personnel opinion information; and generating the abnormal signal detection model by using the second learning data.

12. The method of claim 10, wherein in the transmitting, when the abnormal signal is determined to occur, and the determined abnormal signal occurrence cause type is determined to require an emergency alarm, an emergency warning message and an audible alarm notifying the abnormal signal occurrence and the abnormal signal occurrence cause type are generated and transmitted.

13. The method of claim 1, wherein in the generating of the disease prediction model, a multi-channel respiration sound measurement signal is used as the first learning data.

14. The method of claim 1, in which after the real-time receiving, further comprising:

classifying an abnormal signal occurrence cause type or a specific disease type from the received respiratory mechanics information and biometric signal by using the artificial intelligence model, wherein the artificial intelligence model further includes an abnormal signal detection model trained to classify the abnormal signal occurrence cause type or the specific disease type from input data; and transmitting analysis information including the classified abnormal signal occurrence cause type and specific disease type to the hospital system or the mobile terminal.

15. An integrated monitoring server comprising:

a memory configured to store one or more instructions; and a processor configured to, by executing the one or more instructions:

receive waveform-type respiratory mechanics information from a ventilator of a patient that is installed at a remote location;

receive various biometric signals measured in real time from a patient monitoring device installed at the remote location;

classify presence or absence of a specific disease or a disease type of the patient from the biometric signals by using an artificial intelligence model including a disease prediction model trained to classify the presence or absence of the specific disease or the disease type from input data; and transmit the real-time received waveform-type respiratory mechanics information and analysis information including the presence or absence of the specific disease or the disease type of the patient to a hospital system connected to the server through a dedicated line or a mobile terminal of medical personnel connected to the server through an internet, wherein the disease prediction model is configured to be trained by:

converting a one-dimensional sound type respiration sound measurement signal to a two-dimensional (2D) image;

performing preprocessing of removing a first noise from the converted 2D image; and training the disease prediction model using the preprocessed 2D image as learning data.

16. The server of claim 15, wherein the processor is further configured to perform preprocessing of removing a second noise and process the real-time received respiratory mechanics information and biometric signals into a specified format, wherein the processor is further configured to transmit the preprocessed real-time received respiratory mechanics information and biometric signals.

17. The server of claim 16, wherein the processor is further configured to perform preprocessing of converting the respiratory mechanics information to a health level 7 (HL7) protocol which is a form usable by the hospital system, and output the respiratory mechanics information converted to the HL7 protocol in real time to the data provision unit.

18. The server of claim 16, wherein the processor is further configured to perform data analysis to determine whether the preprocessed data satisfies a threshold value or abnormal symptom condition, wherein the processor is further configured to a visual or audible alarm expressing a data analysis result based on an instruction of the data analysis unit to the mobile terminal of the medical personnel or the hospital system.

19. The server of claim 16, wherein the processor is further configured to an inquiry service for stored data of the patient through a web user interface or a mobile user interface.

20. An integrated monitoring system comprising:

a home ventilator installed at a remote location, and configured to measure respiratory mechanics information of a patient, and transmit the measured respiratory mechanics information in real time;

a hospital ventilator installed in a hospital, and configured to measure the respiratory mechanics information of the patient, and transmit the measured respiratory mechanics information in real time;

a patient monitoring device installed at the remote location and configured to measure a biometric signal including at least one of a respiration sound, heart sound, or electrocardiogram of the patient; and an integrated monitoring server connected to the home ventilator through a network and the hospital ventilator through a dedicated line, and configured to:

receive waveform-type respiratory mechanics information from the home ventilator and hospital ventilator;

receive the biometric signal from the patient monitoring device;

classify presence or absence of a specific disease or a disease type of the patient from the biometric signal by using an artificial intelligence model including a disease prediction model trained to classify the presence or absence of the specific disease or the disease type from input data; and transmit the real-time respiratory mechanics information and analysis information including the presence or absence of the specific disease or the disease type of the patient to a server device of the hospital or a mobile terminal of medical personnel connected thereto through an internet, wherein the disease prediction model is configured to be trained by:

converting a one-dimensional sound type respiration sound measurement signal to a two-dimensional (2D) image;

performing preprocessing of removing a first noise from the converted 2D image; and training the disease prediction model using the prepro-
cessed 2D image as learning data.

21. The system of claim 20, wherein the integrated monitoring server is further configured to perform preprocessing of removing a second noise and
processing the real-time received respiratory mechan-
ics information and the biometric signal into a specified
format, and transmit the preprocessed real-time received respiratory
mechanics information and biometric signal.

22. The system of claim 20, wherein the integrated monitoring server is further configured to perform data analysis to determine whether the prepro-
cessed data satisfies a threshold value or abnormal
symptom condition, and transmit a visual or audible alarm expressing a data
analysis result to the mobile terminal of the medical
personnel or the hospital system.

23. An integrated monitoring server comprising:

a memory configured to store one or more instructions;
and a processor configured to, by executing the one or more
instructions:

receive waveform-type respiratory mechanics informa-
tion from a ventilator of a patient that is installed at
a remote location or various biometric signals mea-
sured in real time from a patient monitoring device
installed at the remote location;

classify an abnormal signal occurrence cause type or a
specific disease type by using an artificial intelli-
gence model trained to classify the abnormal signal
occurrence cause type or the specific disease type
from input data to input the respiratory mechanics
information or the biometric signal to the artificial
intelligence model; and transmit analysis information of the data analysis unit
to a hospital system or a mobile terminal of medical
personnel, wherein the artificial intelligence model includes a disease
prediction model classifying presence or absence of
respiration disease or a respiratory disease type, and wherein the disease prediction model is configured to be
trained by:

converting a one-dimensional sound type respiration
sound measurement signal to a two-dimensional (2D)
image;

performing preprocessing of removing a noise from the
converted 2D image; and training the disease prediction model using the prepro-
cessed 2D image as first learning data.

24. The server of claim 23, wherein the processor is further configured to input the biometric
signal including at least one of a respiration sound,
heart sound, and electrocardiogram of the patient into
the disease prediction model to classify the presence or
absence of the specific disease or disease type of the
patient.

25. The server of claim 23, wherein the artificial intelligence model further includes an abnormal signal detection model trained to classify the
presence or absence of an abnormal signal or the
abnormal signal occurrence cause type from the input
data, and the processor is further configured to input the respiratory
mechanics information into the abnormal signal detec-
tion model to classify the presence or absence of the
abnormal signal or the abnormal signal occurrence
cause type.

26. The server of claim 25, wherein the processor is further configured to generate as second
learning data, pair data including the measured respi-
ratory mechanics information, personal state informa-
tion of the patient, and medical personnel opinion
information, and generate the abnormal signal detec-
tion model by using the second learning data.

27. The server of claim 25, wherein the abnormal signal detection model is configured to the abnormal signal occurrence cause type as one of a
ventilator cause type, an airway cause type, and an
abnormal patient respiration state cause type from the
input data.

28. The server of claim 25, wherein the abnormal signal detection model is configured to the abnormal signal occurrence cause type as probability
information for each of a ventilator cause type, an
airway cause type, and an abnormal patient respiration
state cause type.

* * * * *